US008246957B2

(12) United States Patent
Paul

(10) Patent No.: US 8,246,957 B2
(45) Date of Patent: Aug. 21, 2012

(54) LUPUS ANTIBODIES FOR PASSIVE IMMUNOTHERAPY OF HIV/AIDS

(76) Inventor: Sudhir Paul, Missouri City, TX (US)

(*) Notice: Subject to any disclaimer, the term of this patent is extended or adjusted under 35 U.S.C. 154(b) by 730 days.

(21) Appl. No.: 10/581,295

(22) PCT Filed: Mar. 29, 2004

(86) PCT No.: PCT/US2004/009662
§ 371 (c)(1),
(2), (4) Date: Jun. 1, 2006

(87) PCT Pub. No.: WO2004/087738
PCT Pub. Date: Oct. 14, 2004

(65) Prior Publication Data
US 2007/0105218 A1 May 10, 2007

Related U.S. Application Data

(60) Provisional application No. 60/457,570, filed on Mar. 27, 2003.

(51) Int. Cl.
*C12P 21/08* (2006.01)
*C07K 16/00* (2006.01)
*A61K 39/21* (2006.01)
*A61K 39/42* (2006.01)

(52) U.S. Cl. ............. 424/148.1; 424/408.1; 530/388.35; 530/387.3

(58) Field of Classification Search ........................ None
See application file for complete search history.

(56) References Cited

U.S. PATENT DOCUMENTS

| | | | | |
|---|---|---|---|---|
| 5,445,960 | A | 8/1995 | Masuho et al. | |
| 5,695,927 | A | 12/1997 | Masuho et al. | |
| 5,783,670 | A | 7/1998 | Masuho et al. | |
| 5,807,715 | A | 9/1998 | Morrison et al. | |
| 5,811,238 | A | 9/1998 | Stemmer et al. | |
| 5,952,462 | A | 9/1999 | Powell et al. | |
| 6,156,541 | A * | 12/2000 | Paul et al. | 435/69.6 |
| 6,235,714 | B1 | 5/2001 | Paul et al. | |
| 6,309,880 | B1 * | 10/2001 | Chang et al. | 435/339.1 |
| 6,406,863 | B1 | 6/2002 | Zhu et al. | |
| 6,407,213 | B1 | 6/2002 | Carter et al. | |
| 2003/0078203 | A1 | 4/2003 | Paul et al. | |

FOREIGN PATENT DOCUMENTS

| | | |
|---|---|---|
| WO | WO 2004/087059 | 10/2004 |
| WO | WO 2004/087735 | 10/2004 |
| WO | WO 2004/087738 | 10/2004 |

OTHER PUBLICATIONS

Golding, H. et al. "Identification of homologous regions in human immunodeficiency virus I gp41 and human MHC class II beta 1 domain" J. Exp. Med., Mar. 1988; 167: 914-923.*
Langat DK, et al. "Characterization of antigens expressed in normal baboon trophoblast and cross-reactive with HIV/SIV antibodies." J Reprod Immunol. Jan. 1999;42(1):41-58.*
Bost K. et al. Antibodies against peptides sequence within the HIV envelope protein crossreact with human interleukin-2 Immunological Investigations, 17(6&7):577-586, 1988.*
Gorny MK et al. "Human Monoclonal Antibodies Specific for Conformation-Sensitive Epitopes of V3 Neutralize Human Immunodeficiency Virus Type 1 Primary Isolates from Various Clades". J. Virology, 76(18):9035-9045, 2002.*
Roben P et al. "Recognition properties of a panel of human recombinant Fab fragments to the CD4 binding site of gp120 that show differing abilities to neutralize human immunodeficiency virus type 1." J. Virol. Aug. 1994;68(8):4821-8.*
Nara, P. et al. Curr Drug Targets Infect Disord. Jun. 2005;5(2):157-70.*
Kriangkum, Biomolecular Engineering 18:31-40, 2000.*
Bermas B. et al. "Binding of glycoprotein 120 and peptides from the HIV-1 envelope by autoantibodies in mice with experimentally induced systemic lupus erythematosus and in patients with the disease" AIDS Res. and Human Retroviruses, 10(9):1071-1077, 1994.*
Keller, MA "Passive Immunity in Prevention and Treatment of Infectious Diseases" Clinical Microbiology Reviews, Oct. 2000, p. 602-614 vol. 13, No. 4.*
International Search report, PCT/US04/09399, mailed Jun. 1, 2005.
Written Opinion of the International Searching Authority, PCT/US04/09399, mailed Jun. 1, 2005.
International Search report, PCT/US04/09662, mailed Jun. 28, 2006.
Written Opinion of the International Searching Authority PCT/US04/09662, mailed Jun. 28, 2006.
Paul et al., Specific HIV gp 120-cleaving antibodies induced by covalently reactive analog of gp 120. J. Biol. Chem. May 30, 2003, vol. 278, No. 22, pp. 20429-20435, Mar. 28, 2003.
Nishiyama et al., "Antibodies to the Superantigenic Site of HIV-1 gp 120: Hydrolytic and Binding Aactivities of the Light Chain Subunit" submitted with U.S. Appl. No. 60/857,764, filed Nov. 9, 2006.
"Induction of antibodies to the gp120 superantigenic site by administration of protein A" submitted with U.S. Appl. No. 60/857,764, filed Nov. 9, 2006.

Planque et al., "Naturally Occurring Catalytic IgAs: Protective Anti-HIV Mediators?" submitted with U.S. Appl. No. 60/857,764, filed Nov. 9, 2006.

Planque et al., "Ontogeny of Proteolytic Immunity: IgM Serine Proteases" submitted with U.S. Appl. No. 60/534,689, filed Jan. 8, 2004.

Karle et al., "Selective IgM-Catalyzed Hydrolysis of HIV gp120: An innate defense against gp120?" submitted with U.S. Appl. No. 60/534,689, filed Jan. 8, 2004.

Nishiyama et al., "Toward selective covalent inactivation of pathogenic antibodies" J. Biol. Chem. Feb. 27, 2004, vol. 279, No. 9, pp. 7877-7883, Dec. 15, 2003.

(Continued)

*Primary Examiner* — Bo Peng

(74) *Attorney, Agent, or Firm* — Lucas & Mercanti, LLP; Barry Evans, Esq.

(57) ABSTRACT

Disclosed are monoclonal antibodies and antibody fragments which recognize antigens encoded by HERV DNA sequences, and methods for production, including recombinant antibody fragments derived from lymphoid cells of lupus patients that make antibodies which neutralize HIV.

15 Claims, 13 Drawing Sheets

OTHER PUBLICATIONS

Planque et al., "Broadly Distributed Chemical Reactivity of Natural Antibodies Expressed in Coordination with Specific Antigen Binding Activity" submitted with application in U.S. Appl. No. 60/457,293, filed Mar. 26, 2003.

Karle et al., "HIV-1 Neutralizing Antibody Fragments to a Conserved Envelope Determinant from Lupus Libraries" submitted with application in U.S. Appl. No. 60/457,570, filed Mar. 27, 2003.

Paul et al., "Natural catalytic immunity is not restricted to autoantigenetic substrates: Identification of a human immunodeficiency virus gp 120-cleaving antibody light chain" Appl. Biochem Biotechnol. Jan.-Mar. 2000, vol. 83, No. 1-3, pp. 71-82, Jan. 2000.

Pinto et al. "Panel of anti-gp 120 monoclonal antibodies reacts with same nuclear proteins in uninfected cells as those recognized by autoantibodies from patients with systemic lulus erythematosus" Aids Res. and Hum Retroviruses, Nov. 7, 1994, vol. 10, pp. 823-828.

Fraziano et al., "Epitope specificity of anti-HIV antibodies in human and murine autoimmune diseases" Aids Research and Human Retroviruses, Nov. 6, 1996, vol. 12, No. 6, pp. 491-496.

Root-Bernstein, "Preliminary evidence for idiotype-antidiotype immune complexes cross-reactive with Lymphocyte antigens in AIDS and lupus" Medical Hypotheses (1995) 44, 20-27.

Taguchi et al. "A mechanism-based probe for gp 120-hydrolyzing antibodies" Bioorg. Med. Chem. Lett. 2002, vol. 12, pp. 3167-3170.

\* cited by examiner

```
               1264      1274      1284      1294
                |         |         |         |
gp120 423-432  CAAATTATAAACATGTGGCAGAAAGTAGGAAAA  SEQ ID NO: 1
               ||||||| |||| | | |||||||||||||||
rv_85283       CAAATTAAAAACTTTTTAAAGAAAGTAGGAAAA  SEQ ID NO: 3
```

Figure 2

```
                            Evolutionary integration of viral sequences
                            into host genome is a microbial immune
                                       subversion strategy
                           ↙                              ↘
      Autoimmune host                              Non-autoimmune host
   Ab responses to HERV self-antigens          Tolerance to HERV self-antigens
                    ↓                                       ↓
   Robust Ab responses to present-day          Tolerance to present-day microbes/
   microbes/ Protection against infection          Increased infection
```

Figure 3

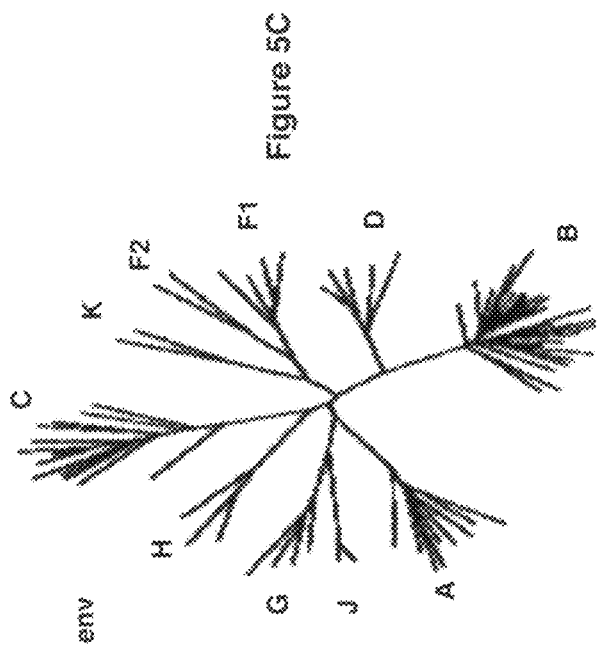

Figure 5A

| NAME | SEQUENCE | SEQ ID |
|---|---|---|
| gp120 (421-436) | KQIINM-WQR-VGKAMY | 48 |
| A.GB.MA245 | KQIINM-WQR-VGKAMY | 49 |
| A.GB.MC108 | KQIINM-WQR-VGKAMY | 50 |
| B.AU.MBC18 | KQIINM-WQR-VGKAMY | 51 |
| B.AU.MBC200 | KQIINM-WQR-VGKAMY | 52 |
| C.BI.BU910112 | KQIINM-WQR-VGKAMY | 53 |
| C.BI.BU910316 | KQIINM-WQR-VGKAMY | 54 |
| D.CD.84ZR085 | KQIINM-WQR-VGKAMY | 55 |
| D.CD.JY1 | KQIINM-WQR-VGKAMY | 56 |
| F.BR.BZ126A | KQIINM-WQR-VGKAMY | 57 |
| F1.BE.VI850 | KQIINM-WQR-VGKAMY | 58 |

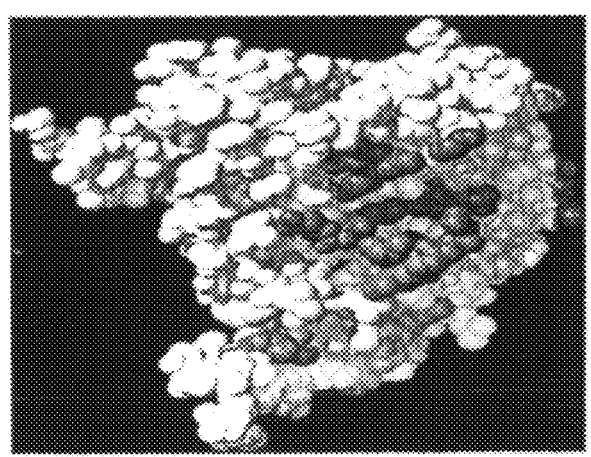

Figure 5C

| NAME | SEQUENCE | SEQ ID |
|---|---|---|
| G.BE.DRBCL | KQIINM-WQR-VGKAMY | 59 |
| H.BE.VI991 | KQIINM-WQR-VGKAMY | 60 |
| J.SE.SE9173 | KQIINM-WQR-VGKAMY | 61 |
| K.CD.EQTB11C | KQIINM-WQR-VGKAMY | 62 |
| N.CM.YBF30 | KQIINM-WQR-VGKAMY | 63 |
| O.CMANT70C | KQIINM-WQR-VGKAMY | 64 |

Figure 5B

Fv variants with improved gp120 binding properties
-- Affinity, avidity, cross-clade HIV neutralization
-- Neutralizing potency consistent with immunotherapy use A. IgG  B. Phage scFv  C. Soluble scFv  D. Multivalent Fv E. IgM  F. Linker-optimized scFv  G. Hybrid/affinity matured scFv VH: Anti-gp120/mutated

Figure 6 scFv JL413 VL domain

1   ASP VAL VAL MET THR GLN SER PRO SER SER VAL SER ALA SER VAL GLY ASP ARG VAL THR
21  ILE THR CYS ARG ALA SER GLN GLY ILE GLY ASN TRP LEU ALA TRP TYR GLN GLN LYS PRO
41  GLY LYS ALA HIS ASN LEU LEU ILE TYR GLY ALA SER SER LEU GLN SER GLY VAL PRO SER
61  ARG PHE SER GLY SER GLY SER GLY THR ASP PHE THR LEU THR ILE SER SER LEU GLN PRO
81  GLU ASP SER ALA THR TYR TYR CYS GLN GLN ALA LEU VAL GLY THR PHE GLY GLY GLY THR
101 LYS VAL GLU ILE LYS ARG      SEQ ID NO: 46 scFv JL413 VL domain

1   GLN VAL ASN LEU ARG GLU SER GLY PRO GLY LEU VAL LYS PRO SER GLU THR LEU SER LEU
21  THR CYS THR VAL SER GLY GLY PHE ILE SER SER TYR ILE SER TRP SER TRP ILE ARG GLN PRO
41  PRO GLY LYS GLY LEU GLU TRP VAL SER ARG VAL TYR ILE GLY ARG SER GLY SER HIS THR ASN TYR
61  PRO SER LEU LYS SER ARG VAL THR ILE SER VAL ASP THR SER LYS ASN GLN PHE SER LEU
81  LYS LEU SER SER VAL THR ALA ALA ASP THR ALA MET TYR CYS TYR CYS TRP GLY GLN GLY
101 THR LEU VAL THR VAL SER SER      SEQ ID NO: 47

Figure 10A scFv JL427 VL domain

1   GLN SER VAL LEU THR GLN PRO PRO SER VAL SER GLY ALA PRO GLY GLN ARG VAL THR ILE   60
21                                      CDR1
21  SER CYS SER GLY SER SER SER ASN PHE GLY LEU ASN TYR VAL TYR TRP TYR GLN HIS PHE
41  PRO GLY THR ALA PRO LYS LEU LEU ILE TYR ARG ASN ASP GLN ARG PRO LEU GLY VAL PRO
61  ALA ARG PHE SER GLY SER LYS SER GLY THR SER ALA SER LEU ALA ILE SER GLY LEU ARG
81  SER GLU ASP GLU ALA ASP TYR TYR CYS GLN SER TYR ASP ASN SER LEU SER GLY TRP VAL
121 PHE GLY GLY GLY TYR GLN LEU TYR VAL LEU GLY     SEQ ID NO: 44 scFv JL427 VL domain

1   GLN VAL GLN LEU GLN GLN SER GLY GLY GLY LEU VAL GLN PRO GLY ARG SER LEU ARG LEU   60
21  SER CYS ALA ALA SER GLY PHE THR PHE SER SER TYR ILE GLY ARG PHE VAL ARG GLN ALA
41  PRO GLY LYS GLY LEU GLU TRP VAL SER TYR ILE SER TYR SER GLY MET HIS TRP VAL ARG GLN ALA
61  ALA ASP SER VAL LYS GLY ARG PHE THR ILE SER ARG ASP ASN SER LYS ASN THR LEU TYR
101 LEU GLN ILE ASN SER LEU ARG ALA GLU ASP THR ALA VAL TYR TYR CYS ALA ARG GLY LEU
121 PRO ASN TYR GLY MET ASP ILE TRP GLY GLN GLY THR THR VAL THR VAL SER SER  SEQ ID NO: 45

Figure 10B

Light chain SK18 VL domain

1
ASP ILE GLN MET THR GLN SER PRO SER SER LEU SER ALA SER VAL GLY ASP ARG VAL THR

21
VAL THR CYS ARG ALA SER GLN SER ILE SER SER TYR LEU ASN TRP TYR GLN GLN PRO

41
GLY LYS ALA PRO LYS LEU LEU ILE TYR ALA ALA SER SER LEU GLN SER GLY VAL PRO SER
                                                                              80
61
ARG PHE SER GLY SER GLY SER GLY THR ASP PHE THR LEU THR ILE SER SER LEU GLN PRO

81
GLU ASP PHE ALA THR RYR PHE CYS GLN GLN SER TYR SER ILE PRO ARG THR PHE GLY GLN

101
GLY THR LYS VAL GLU ILE LYS     SEQ ID NO: 43

Figure 10C

LUPUS ANTIBODIES FOR PASSIVE IMMUNOTHERAPY OF HIV/AIDS

This application is a 371 of PCT/US04/09662 filed Mar. 29, 2004 which claims priority to and the benefit of U.S. Provisional Patent Application No. 60/457,570 filed Mar. 27, 2003, the contents of which are incorporated herein by reference in their entirety.

U.S. Government grants AI046029, CA080312, HL094126, and HL059746 contributed to the development of this technology.

Pursuant to 35 U.S.C. §202(c) it is acknowledged that the U.S. Government has certain rights in the invention described herein, which was made in part with funds from the National Institutes of Health, Grant Numbers: HL59746, AI31268 and AI46029.

FIELD OF THE INVENTION

Preparation and use of antibodies that bind microbial antigens, more particularly a conserved determinant of gp120 and neutralize HIV, for the purposes of immunotherapy and immunoprophylaxis against HIV.

BACKGROUND

Antibodies (Abs) contain variable (V) domains at which contacts with antigens are established. The nature and number of these contacts determines the binding specificity of Abs. The human Ab repertoire, defined as the number of Abs with different V domain sequences, is estimated at $10^{11}$-$10^{12}$, each with a potentially different antigen binding specificity.

Recent developments in molecular biology have enabled the development of novel methods whereby medically useful Abs can be isolated from the natural human repertoire and can be improved further by protein engineering techniques. An appreciation of Ab structural organization is helpful in appreciating the scope of the present invention, and a brief review of this aspect follows.

Contacts with antigen epitopes occur mainly at the complementarity determining regions (CDRs) and to a lesser extent the framework regions (FR) of Abs (FIG. 1). Ab diversity is generated by the following processes: (a) inheritance of about 50 germline genes encoding the V domains of each of the two Ab subunits, the light (L) and heavy (H) chains; (b) combinatorial diversity brought about by linkage of different L and H chains within the Ab structure; (c) junctional diversity generated during recombination of the V and joining (J) gene segments of the L chain, and the V, diversity (D) and J gene segments of the H chain; and (d) rapid mutation occurring in the complementarity determining regions over the course of B cell clonal selection, a process entailing binding of the antigen to Abs expressed as components of the B cell receptor (BCR), and resulting in stimulation of division of the B cells expressing BCRs with the highest binding affinity. An additional level of diversity is offered by the use of different constant domains by Abs, that is, the $\mu$, $\delta$, $\gamma$, $\alpha$ and $\epsilon$ regions of the H chain and the $\kappa$ and $\lambda$ chains of the L chain. Early in the ontogeny of the immune response, Abs contain $\mu$ or $\iota$ constant regions. Later, isotype switching occurs, and the $\mu/\delta$ regions are replaced by $\gamma/\alpha/\epsilon$ in more differentiated Abs.

The purpose of Abs made by the healthy immune system is to protect against pathogens. Such Ab responses are usually mounted upon exposure to foreign antigens, e.g., in microbial infection. However, in some cases the human immune system makes Abs that react with some foreign antigens even without prior exposure to the foreign antigen. For example, Abs to viral antigens are found in patients with autoimmune disease without evidence of infection, e.g., e.g., Abs to human T lymphotropic virus (HTLV-1) in lupus patients and Abs to certain retroviral antigens in multiple sclerosis. In the case of HIV-1, uninfected patients with lupus or with mixed connective tissue disease are known to express Abs to the envelope protein of the virus (1,2).

In many cases, the protective immune responses against microbes in infected subjects are insufficient to control infection. This occurs, for example, in humans who are immunodeficient. Furthermore, many microbes use immune subversion mechanisms to establish infection, with the result that infected individuals produce Abs that do not protect adequately in the spread of infection. Monoclonal Abs to microbial proteins that can be administered to such individuals as passive immunotherapeutic reagents could provide protection against infection.

In the present invention, patients with autoimmune disease are identified as a source of such monoclonal Abs. The unique properties of the anti-microbial Abs from patients with autoimmune disease are likely due, in part to their unique genesis. These Abs are produced on account of enhanced autoreactive immunological responses. The autoantigens serving as targets of immune responses include polypeptides derived from endogenous retroviral (ERV) sequences found in the heritable genome of higher organisms, some of which are homologous in sequence to modem-day microbial antigens. Between 1% and 8% of the human genome is composed of ERVs (HERVs), which are thought to have been acquired gradually over the course of evolution. The human genome contains about 3 billion bases, of which about 3% are expressed. There is extensive evidence that retroviral sequences are expressed in autoimmune diseases, and this process has been proposed as a mechanism underlying pathogenic autoimmune responses (reviewed in 3,4).

REFERENCES

1. Bermas, B. L., Petri, M., Berzofsky, J. A., Waisman, A., Shearer, G. M. and Mozes, E. Binding of glycoprotein120 and peptides from the HIV-1 envelope by autoantibodies in mice with experimentally induced systemic lupus erythematosus and in patients with the disease. *AIDS Res Hum Retroviruses.* 10:1071-1077, 1994.
2. Douvas, A., Takehana, Y., Ehresmann, G., Chernyovskiy, T. and Daar, E. S. Neutralization of HIV type 1 infectivity by serum antibodies from a subset of autoimmune patients with mixed connective tissue disease. *AIDS Res Hum Retroviruses.* 12:1509-1517, 1996.
3. Nelson, P. N., Carnegie, P. R., Martin, J., Davari Ejtehadi, H., Hooley, P., Roden, D., Rowland-Jones, S., Warren, P., Astley, J. and Murray, P. G. Demystified—Human endogenous retroviruses. *Mol Pathol.* 56:11-18, 2003.
4. Urnovitz, H. B. and Murphy, W. H. Human endogenous retroviruses: nature, occurrence, and clinical implications in human disease. *Clin Microbiol Rev.* 9:72-99, 1996.

SUMMARY OF THE INVENTION

One object of the invention is to provide a monoclonal Ab or fragment thereof from organisms with autoimmune disease which recognize viral antigens and neutralize virus infectious capability.

Another object is to provide a monoclonal Ab of fragment thereof that recognizes the antigenic polypeptide products and homologs thereof encoded by human endogenous retroviral sequences (HERVs).

Another object is to provide a monoclonal Ab or fragment thereof that neutralizes HIV-1 derived from patients with systemic lupus erythematosus.

Another object is to provide a monoclonal Ab or fragment thereof that recognizes an antigenic epitope of HIV-1 homologous to a HERV polypeptide that neutralizes HIV-1.

Another object is to provide cell lines from lymphoid cells of lupus patients, which produces Abs that bind to an antigenic epitope of HIV-1 homologous to a HERV polypeptide that neutralizes HIV-1.

DESCRIPTION OF DRAWINGS

FIG. 2: Homology of the consensus nucleotide sequence encoding gp120 residues 422-432 with HERV rv_85283. Identities (|).

FIG. 3: Concept of protective antibody responses to microbes in patients with autoimmune disease owing to breakdown of tolerance to HERV peptide products.

FIG. 5: A, Structure of CD4 binding site of gp120. Contact and proximate residues in the CD4 binding site are shown in red and green. Residues 421-436 are shown in cyan and green. From Kwong et al., *Nature* 393:648-659, 1998. B, Homology at residues 421-436 in selected group M HIV subtypes. C, Inter-clade HIV-1 relationships determined by envelope homology analysis.

FIG. 6: Single chain Fv (scFv) and its examples of its engineered variants. Shown are the VL and VH components of IgG, designated Fv (A); the Fv expressed as a fusion protein on the surface of M13 phages (B), soluble Fv isolated from the periplasm or culture supernatant of bacteria, some of which can form intermolecular aggregates (C), the Fv assembled as a tetravalent bundle (D) or recloned as IgM (E) to increase binding avidity, the Fv containing a linker that is optimized to allow improved interfacial VL-VH pairing and reduce aggregation as needed (F), and affinity matured Fv obtained by combinatorial VL-VH diversification and CDRH3 mutagenesis in vitro (G).

FIG. 10: Deduced V domain amino acid sequences of gp120 binding clones isolated from lupus patients. Complementary determining regions (CDRs) are highlighted. A, Fv JL413; B, Fv JL427; C, L chain SK18

DESCRIPTION OF THE INVENTION

Figure 1:
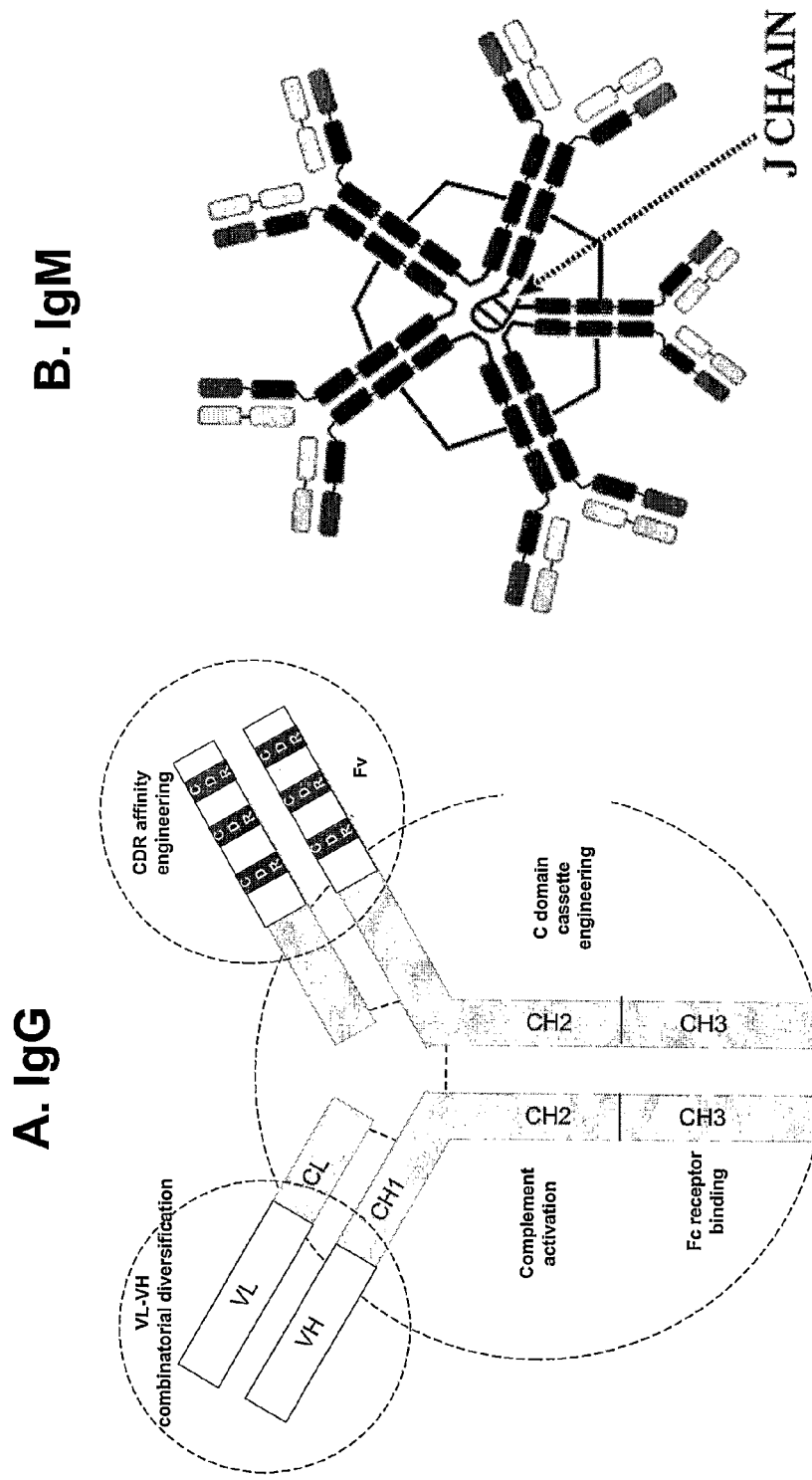
FIG. 1: Schematic diagrams of an IgG antibody (A) and IgM (B). The CDRs contain the majority of antigen-contacting amino acids. Mutations can be introduced into the CDRs to improve antigen binding affinity. Combinatorial VL-VH diversification is an additional means to improve antigen-recognition properties. Heavy chain constant region domains are responsible for antigen-stimulated effector functions. cDNAs from cloned antibody V domain repertoires are inserted into vectors containing the heavy and light chain constant domains, allowing expression of full-length antibody molecules. IgM antibodies are pentameric structures presenting a total of 10 antigen binding sites. The monomers are held together by S—S and the J (joining) chain. IgA antibodies (not shown) are dimeric structures containing four antigen binding sites, held together by the S (secretory) piece.

1. Endogenous Retroviral Antigens as Stimulants of Abs to Foreign Antigens in Autoimmune Disease Polyclonal Abs to HIV gp120 are present have been detected in the sera of patients with lupus and mixed connective tissue disease (1,2). The Abs to found in sera from lupus patients are of interest as protective factors against HIV infection, as they bind at a comparatively conserved determinant of gp120 composed residues 421-436 [hereafter designated gp120(421-436)]. However, a study using a synthetic peptide corresponding to gp120(421-436) as immunogen in experimental animals reported that Abs to this peptide display no HIV-1 neutralizing activity (3). Consequently, there has been little interest in developing such Abs for passive immunotherapy of HIV-1 infection.

Synthetic peptides do not necessarily fold into the conformation adopted by the corresponding peptide epitopes found as components of larger proteins. Therefore, the results with experimentally induced Abs to gp120(421-436) does not predict the properties of naturally occurring Abs to this region of gp120 found in lupus patients. The clinical literature contains anecdotal evidence suggests the possibility of a negative correlation between HIV-1 infection and lupus (4,5). However, no controlled epidemiological studies have been conducted to establish whether patients with lupus are at lower risk of contracting HIV-1 infection or developing AIDS.

TABLE 1

Identification of a HERV sequence element homologous to the consensus nucleotide sequence encoding residues 422-432 (nucleotides 1249-1281).

| Query | Nucleotide identity/ total nucleotides | HERV identity | Chromosome location |
|---|---|---|---|
| C | 27/33 | rv_85283 | chromosome Xq13.3-21.2 |
| D | 27/33 | rv_85283 | chromosome Xq13.3-21.2 |

Database homology searches were carried out using query sequences A-D as follows:
A 5'-aaacaaattataaacatgtggcaggaagtaggaaaagcaatgtatgcc-3'
B 3'-tttgtttaatatttgtacaccgtccttcatccttttcgttacatacgg-5'
C 3'-ccgtatgtaacgaaaaggatgaaggacggtgtacaaatattaaacaaa-5'
D 5'-ggcatacattgcttttcctacttcctgccacatgtttataatttgttt-3'
Initial searches were done using the HERV database http://HERVing.cas.cz)
The four query sequences correspond to all four insertion orientations into the two host DNA strands. Query A and B yielded no hit. Identities value correspond to the region of best match. Chromosomal location was confirmed by repeat searches using Genbank. No homologies between the queries and known expressible human proteins was obtained in these searches.

Immune responses to endogenous retroviral (ERV) sequence polypeptides occur frequently in patients with autoimmune disease. The inciting immunogen for formation of Abs to gp120 by lupus patients is not known. We conducted database searches for endogenous human antigens expressing homology with the nucleotide sequence coding gp120 residues 421-436, the epitope recognized by the lupus Abs. No detectable homology with conventional human antigens was detected. Homology between certain self antigens [HLA class I heavy chains, VIP and neurolikin] are known (6-8), but these homologies do not fall within gp120 residues 431-436.

Searches in a newly available human endogenous retroviral (HERV) sequence database (9) identified a sequence displaying unmistakable homology with the gp120 422-432 region. This HERV is located on chromosome X. By searching the human endogenous retroviral (HERV) sequence database (9), we identified a HERV sequences located in chromosome X displaying homology with this region of gp120 (GenBank number AL592563.7; Table 1; FIG. 2). Two additional HERV sequences with homology to the 421-436 region of gp120 were evident. These sequences correspond to nucleotides 1394-1443 of a HERV-L family member and nucleotides 1254-1304 of another HERV-L family member, but the alignments contained 1 and 4 nucleotide gaps, respectively. Translated into the polypeptide sequence, the HERV element shown in FIG. 2 display identities at 8 of 15 gp120 amino acid positions, and 5 of the 7 mutations involve chemically similar amino acids according to the scale of Grantham (24). Gp120 residues 429-436 displayed homology with HERV element rv_062846 (GenBank AL391989.9; 4/8 amino acid identities; 2/4 mutations involve chemically similar amino acids; nucleotide identities corresponding to this region of gp120, 17/24).

Most HERVs were originally identified by the human genome sequencing project, which sequenced the DNA of only a few individuals. HERVs are highly susceptible to sequence divergence in different human subpopulations. Moreover, nonexpressible HERVs are known to be rendered expressible by mutation and transposition events in autoimmune disease (10,11). This leaves open the possibility that lupus patients may express gp120-related HERVs distinct from the general population. HERVs are found integrated in genome in the sense and anti-sense orientations. These can be fragments or full-length viral genes (12). HERVs are often located adjacent to expressed genes and fulfill a regulatory function. The long terminal repeats characteristic of HERV sequences often encompass promoters and enhanced (10,11). Other HERV sequences are expressed as polypeptides and fulfill essential biological functions, e.g., syncytin, a HERV-encoded protein that mediates cytotrophoblast fusion into the syncytial trophoblast in the placenta (13). The majority of HERV sequences are yet to be assigned their biological function. HERV sequences containing nonsense codons can be converted into expressible genes in lupus patients by stop codon inactivating mechanisms (14) such as replacement mutations, deletions and insertions. Expression of HERVs in PBMCs of different individuals is highly variable (15) and HERV expression can be tissue-selective (10). Increased HERV expression in lupus is reported (16), and production of Abs to HERV encoded polypeptides has been described in lupus patients (17). These Abs may cross react with self antigens such as Sm and snRNP (18); and HERV sequences are suggested to function as T cell superantigens (19). Links between HIV and HERVs are evident from these observations: sequence homology between the junctional HIV gp41-gp120 env region and a HERV element homologous (20); sequence and functional homology between a HERV-K polypeptide and the HIV Rev protein (21); and, binding of anti-HIV Abs to polypeptides in baboon placenta thought to be ERV-encoded (22).

From an evolutionary perspective, HERV sequences may fulfill a beneficial role, in that transpositions and mutations of these sequences probably facilitates emergence of proteins with new functions. On the other hand, frequent HERV involvement in autoimmune disease may be due to lack of immune tolerance to the new proteins. In comparison, immune tolerance to ancient proteins has presumably developed gradually over the course of evolution. HERV sequences are more susceptible to 'genetic drift' than conventional expressed proteins, and production of differing HERV-products in different subjects remains possible. As noted previously, HERV expression is often increased in patients with autoimmune disease compared to the general population. This may be explained by genetic changes in individual germ cells that convert HERV sequences from nonexpressed to expressed elements, e.g., via stop codon inactivating mechanisms.

2. Isolation of Homogeneous Ab Fragments to gp120 Residues 421-436

In view of the foregoing considerations, we explored the determinant composed of residues 421-436 as a target of Abs to HIV. Table 2 shows the extent to which the amino acid sequence of this epitope is conserved in diverse HIV-1 strains. The frequency of the consensus amino acids in each of the positions is better than 80% except for residues 424, 429 and 432. This region of gp120 is one of the most conserved potential targets of Abs.

TABLE 2

Frequencies of consensus amino acids in gp120 residues 421-436.

| Residue | 421 | 422 | 423 | 424 | 425 | 426 | 427 | 428 | 429 | 430 | 431 | 432 | 433 | 434 | 435 | 436 |
|---|---|---|---|---|---|---|---|---|---|---|---|---|---|---|---|---|
|  | Lys | Gln | Ile | Ile | Asn | Met | Trp | Gln | Glu | Val | Gly | Lys | Ala | Met | Tyr | Ala |
| Strains, # | 349 | 380 | 355 | 251 | 331 | 319 | 379 | 367 | 158 | 333 | 373 | 161 | 366 | 324 | 382 | 377 |
| Freq, % | 91 | 99 | 92 | 65 | 86 | 83 | 99 | 96 | 41 | 87 | 97 | 42 | 95 | 84 | 99 | 98 |

Number of strains from which the consensus was derived is indicated (all strains available in the Los Alamos database). Frequency refers to: (# of strains expressing the indicated residue x 100/total # of strains).

Example I explains our reasoning for using lupus patients as the source of human monoclonal Abs to this region of gp120. As described therein, HIV-1 infected individ Ab fragments. The mutants are then expressed on the surface of a display vector as described above and allowed to bind the virus or a pure viral antigen. This allows separation of the mutants with the highest virus binding affinity, which in turn can be anticipated to result in improved virus neutralization capacity. The mutagenesis process for the VL and VH domains improves the antigen binding strength on account of establishment of improved contacts with the antigen. The mutagenesis of the linker peptide that joins the VL and VH domains is designed to improve the interfacial contacts of the VL and VH domains, which allows these domains to forn superior antigen binding cavities.

The VL domain obtained from lupus Abs can be paired with the VH domain of other Abs directed to gp120, e.g., the known human Abs clones b12, S1-1 and F105. This can improve the binding strength to the virus and also result in changes in epitope specificity that can improve the virus neutralizing activity.

3. Identification of Novel Abs by Screening for BERV Binding

As disclosed herein, Abs that recognize HERV polypeptides may fulfill a protective function against modern-day microbes. The theoretical underpinning for this expectation is that expression of HERV sequences has become an integral component of host-microbe relationships over the course of evolution. In this theory, we conceive that the key nucleic acid sequences of microbes encoding polypeptides against which host organisms can mount protective immune responses are integrated into the host genome as a subversion mechanism. Once integrated into the host genome any expressed HERV sequences are treated by the host immune system as self-antigens, and tolerance to HERV antigens (and to important microbial antigenic epitopes) develops in the course of normal tolerogenic mechanisms in the developing immune system that limit the immune responses to self-antigens. These mechanisms consist of various antigen-directed T and B cell clonal silencing and abortion events that are directed at precluding autoimmune disease. Under physiological circumstances in organisms without autoimmune disease, the presence of HERVs may be conceived, therefore, as a mechanism used by microbes to impair host cell immune responses, allowing infections to occur more readily.

In autoimmune disease, on the other hand, there is a breakdown in tolerance to self-antigens. Consequently, tolerance to HERV polypeptide products also breaks down, and protective Abs are apparent in patients with autoimmune disease. These concepts are illustrated schematically in FIG. 3.

Accordingly, identification of Abs that bind HERV polypeptides specifically is a novel route to obtaining protective anti-microbial Abs that are useful for immune therapy applications. A preferred source of such Abs is patients with autoimmune disease. Certain methods to identify anti-HERV Abs are described in Example IV, and other methods can be conceived that yield the same result. An outline of the strategy is as follows:

HERV sequences with homology to modern-day microbial proteins are identified by database searches, available, for example at Blastn and the HERV database, herv.im-q.cas.cz. DNA sequences corresponding to antigenic epitopes 5-7 of the microbial antigenic target are first identified, as the minimum length of an antigenic epitope is generally thought to be 5-7 amino acids (15-21 nucleotides). The epitope to be targeted is generally selected based on its functional importance. For example, in the case of HIV, it is beneficial to choose an antigenic epitope blockade of which can be expected to result in inhibition of binding to host cell CD4 receptors, and, consequently, inhibition of viral entry into host cells. The level of statistical significance for determination of homology with the query sequence depends on several factors, including the number of nucleotides that are identical to the query and the number of gaps that in the identities. Several software programs are available to judge the significance of the homology (e.g., ref 23). Equally important when assessing homology is the likelihood of structurally similarity between the query peptide epitope and the HERV peptide epitope. For example, dissimilarities at certain amino acids can result in large structural changes, e.g., introduction of a Pro residue can disrupt the helical structure of an epitope. Reference 24 describes an algorithm to assess peptide sequences based on the chemical similarity of their component amino acids. This algorithm can be employed to identify the best HERV candidate antigens for the isolation of Abs.

Abs that bind the HERV antigenic peptide are isolate using Ab repertoires displayed on a suitable vector as described in the preceding section. Alternatively, cell lines can be prepared from the lymphocytes of the donor organism by transformation with Epstein-Barr virus or by forming hybridomas using a myeloma cell line, and the Abs secreted by the cell lines can be tested for binding to the HERV peptide by conventional immunoassay methods.

Once the HERV peptide-binding Abs have been isolated, they are analyzed for their ability to block microbial infection. In the case of HIV, for example, PBMCs are used as hosts and the infection is measured based on determination of the HIV antigen p24.

4. Administration of Antibodies

The Abs described herein are generally administered to a patient as a pharmaceutical preparation.

The pharmaceutical preparations of the invention are conveniently formulated for administration with an acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the Abs in the chosen medium will depend on the hydrophobic or hydrophilic nature of the medium, as well as the other properties of the Abs. Solubility limits may be easily determined by one skilled in the art.

As used herein, "biologically acceptable medium" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional media or agent is incompatible with the Ab to be administered, its use in the pharmaceutical preparation is contemplated.

Conventional passive immunization methods are be employed when administering the Abs. In a preferred embodiment, Abs will be infused intravenously into the patient. For treatment of certain medical disorders, steps must be taken to ensure that sufficient amounts of the molecules reach their target cells to exert a biological effect.

The lipophilicity of the molecules, or the pharmaceutical preparation in which they are delivered may have to be increased so that the molecules can arrive at their target locations. Furthermore, the Abs of the invention may have to be delivered in a cell-targeted carrier so that sufficient numbers of molecules will reach the target cells.

Methods for increasing the lipophilicity and targeting of therapeutic molecules, which include capsulation of the Abs of the invention into Ab studded liposomes, are known in the art.

The Abs that are the subject of the present invention can be used as Ab fragments or whole Abs or they can be incorporated into a recombinant molecule or conjugated to a carrier such as polyethylene glycol. In addition any such fragments or whole Abs can be bound to carriers capable of causing the transfer of said Abs or fragments across cell membranes as mentioned above.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

The pharmaceutical preparation comprising the Abs may be administered at appropriate intervals, for example, twice a week until the pathological symptoms are reduced or alleviated, after which the dosage may be reduced to a maintenance level. The appropriate interval in a particular case would normally depend on the condition and the pathogenic state sought to be treated in the patient.

The Abs suitable for passive immunotherapy will fulfill the standard criteria for acceptable prophylactic or therapeutic agents: (1) Binding of the target peptide antigen by the Abs will lead to a beneficial change in a pathological process by either functionally inactivating the target peptide antigen; and (2) Administration of said Abs will result in a favorable therapeutic index such that the clinical benefit gained outweighs the morbidity associated with any side-effects. Discussions of how such criteria are established for the acceptability of prophylactic or therapeutic agents are common in the art can be found in such texts as *Guide to Clinical Trials* by Bert Spilker, Raven Press, New York, 1991. Acceptable criteria for demonstration of efficacy include, for example, in the case of tumor therapy, a reduction in tumor volume, time to progression and improved survival. In the case of HIV immunotherapy, efficacy is determined by measuring viral burden in the blood, CD4+ T cell counts and the incidence of opportunistic infections.

Conventional monoclonal Abs that act to inhibit the function of particular target molecules are among the most common type of therapeutic agent under development for clinical use by biotechnology and pharmaceutical companies. Some of these have shown substantial clinical promise. For example, in the field of organ transplantation, an Ab (OKT3) which binds to the T cell receptor has been employed to deplete T cells in vivo. Additionally, Abs are being used to treat graft v. host disease with some success. A clinical trial has been established which is assessing the ability of anti-CD4 Ab to deplete a subset of T cells in the treatment of multiple sclerosis. Accordingly, methods of administration of Abs are well known to clinicians of ordinary skill in the art.

The HERV peptides disclosed in the present invention can also potentially be used as prophylactic vaccines designed to elicit protective Ab responses against the desired antigens. For example, the peptides can mixed with a suitable adjuvant formulation such as alum can be administered intramuscularly at a dose optimized for maximum Ab synthesis, and two or three booster injections can be administered at 4 week intervals, until the Ab concentration in the serum reaches plateau levels. The protective immunity so generated is anticipated to last for several years, because vaccination will result in formation of specific, long lived memory cells that can be stimulated to produce Abs upon exposure to the offending organism. Descriptions and methods to determine the Ab concentrations are set forth in the Examples. Because Ab synthetic response to most antigens are T cell dependent, an appropriate T cell epitope can be incorporated into the immunogen by peptide synthesis. Alternatively, a carrier such as keyhole limpet hemocyanin can be conjugated to the HERV peptide vaccine via coupling through Lys side chain amino groups or Cys side chain sulfahydryl groups to maximize the Ab response if necessary.

While certain of the preferred embodiments of the present invention have been described and specifically exemplified above, it is not intended that the invention be limited to such embodiments. Various modifications may be made thereto without departing from the scope and spirit of the present invention. The following examples are provided to facilitate an understanding of the present invention.

REFERENCES

1. Bermas, B. L., Petri, M., Berzofsky, J. A., Waisman, A., Shearer, G. M. and Mozes, E. Binding of glycoprotein120 and peptides from the HIV-1 envelope by autoantibodies in mice with experimentally induced systemic lupus erythematosus and in patients with the disease. *AIDS Res Hum Retroviruses*. 10:1071-1077, 1994.
2. Douvas, A., Takehana, Y., Ehresmann, G., Chernyovskiy, T. and Daar, E. S. Neutralization of HIV type 1 infectivity by serum antibodies from a subset of autoimmune patients with mixed connective tissue disease. *AIDS Res Hum Retroviruses*. 12:1509-1517, 1996.
3. Morrow, W. J., Williams, W. M., Whalley, A. S., Ryskamp, T., Newman, R., Kang, C. Y., Chamat, S., Kohler, H. and Kieber-Emmons, T. Synthetic peptides from a conserved region of gp120 induce broadly reactive anti-HIV responses. *Immunol*. 75:557-564, 1992.
4. Wallace, D. J. Lupus, acquired immunodeficiency syndrome and antimalarial agents. *Arthritis Rheum*. 34:372-373, 1991.
5. Daikh, B. E. and Holyst, M. M. Lupus-specific autoantibodies in concomitant human immunodeficiency virus and systemic lupus erythematosus: case report and literature review. *Semin Arthrisis Rheum*. 30:418-425, 2001.
6. De Santis, C., Robbioni, P., Longhi, R., Lopalco, L., Siccardi, A. G., Beretta, A. and Roberts Jr., N. J. Cross-reactive response to human immunodeficiency virus type 1 (HIV-1) gp120 and HLA class I heavy chains induced by receipt of HIV-1-derived envelope vaccines. *J Infect Dis*. 168:1396-1403, 1993.
7. Pert, C. B., Hill, J. M., Ruff, M. R., Berman, R. M., Robey, W. G., Arthur, L. O., Ruscetti, F. W. and Farrar, W. L. Octapeptides deduced from the neuropeptide receptor-like pattern of antigen T4 in brain potently inhibit human immunodeficiency virus receptor binding and T-cell infectivity. *Proc Natl Acad Sci USA*. 83:9254-9258, 1986.
8. Lee, M. R., Ho, D. D. and Gurney, M. E. Functional interaction and partial homology between human immunodeficiency virus and neuroleukin. *Science*. 237:1047-1051, 1987.
9. Pačes, J., Pavlíček, A. and, Páces, V. HERVd: database of human endogenous retroviruses. *Nucleic Acids Res*. 30:205-206, 2002.
10. Nelson, P. N., Carnegie, P. R., Martin, J., Davari Ejtehadi, H., Hooley, P., Roden, D., Rowland-Jones, S., Warren, P., Astley, J. and Murray, P. G. Demystified—Human endogenous retroviruses. *Mol Pathol.* 56:11-18, 2003.

11. Urnovitz, H. B. and Murphy, W. H. Human endogenous retroviruses: nature, occurrence, and clinical implications in human disease. *Clin Microbiol Rev.* 9:72-99, 1996.

12. Lower, R., Lower, J. and Kurth, R. The viruses in all of us: characteristics and biological significance of human endogenousretrovirus sequences. *Proc Natl Acad Sci USA.* 93:5177-5184, 1996.

13. Mi, S., Lee, X., Li, X., Veldman, G. M., Finnerty, H., Racie, L., LaVallie, E., Tang, X.Y., Edouard, P., Howes, S., Keith, J. C. Jr. and McCoy, J. M. Syncytin is a captive retroviral envelope protein involved in human placental morphogenesis. *Nature.* 403:785-789, 2000.

14. Ogasawara, H., Hishikawa, T., Sekigawa, I., Hashimoto, H., Yamamoto, N. and Maruyama, N. Sequence analysis of human endogenous retrovirus clone 4-1 in systemic lupus erythematosus. *Autoimmuntity.* 33:15-21, 2000.

15. Krieg, A. M., Gourley, M. F., Klinman, D. M., Perl, A. and Steinberg, A. D. Heterogeneous expression and coordinate regulation of endogenous retroviral sequences in human peripheral blood mononuclear cells. *AIDS Res Hum Retroviruses* 8:1991-1998, 1992.

16. Ogasawara, H., Naito, T., Kaneko, H., Hishikawa, T., Sekigawa, I., Hashimoto, H., Kaneko, Y., Yamamoto, N., Maruyama, N. and Yamamoto, N. Quantitative analyses of messenger RNA of human endogenous retrovirus in patients with systemic lupus erythematosus. *J Rheumatol.* 28:533-538, 2001.

17. Bengtsson, A., Blomberg, J., Nived, O., Pipkorn, R., Toth, L. and Sturfelt, G. Selective antibody reactivity with peptides from human endogenous retroviruses and nonviral poly(amino acids) in patients with systemic lupus erythematosus. *Arthritis Rheum.* 39:1654-1663, 1996.

18. Blomberg, J., Nived, O., Pipkorn, R., Bengtsson, A., Erlinge, D. and Sturfelt, G. Increased antiretroviral antibody reactivity in sera from a defined population of patients with systemic lupus erythematosus. Correlation with autoantibodies and clinical manifestations. *Arthritis Rheum.* 37:57-66, 1994.

19. Woodland, D. L. Immunity and retroviral superantigens in humans. *Trends Immunol.* 23:57-58, 2002.

20. Horwitz, M. S., Boyce-Jacino, M. T. and Faras A. J. Novel human endogenous sequences related to human immunodeficiency virus type 1. *J Virol.* 66:2170-2179, 1992.

21. Lower, R., Tonjes, R. R., Korbmacher, C., Kurth, R. and Lower, J. Identification of a Rev-related protein by analysis of spliced transcripts of the human endogenous retroviruses HTDV/HERV-K. *J Virol.* 69:141-149, 1995.

22. Langat, D. K., Johnson, P. M., Rote, N. S., Wango, E. O., Owiti, G. O., Isahakia, M. A. and Mwenda, J. M. Characterization of antigens expressed in normal baboon trophoblast and cross-reactive with HIV/SIV antibodies. *J Reprod Immunol.* 42:41-58, 1999.

23. Pesole, G., Liuni, S. and D'Souza, M. PatSearch: A pattern matcher software that finds functional elements in nucleotide and protein sequences and assesses their statistical significance. *Bioinformatics.* 16:439-50, 2000.

24. Grantham, R. Amino acid difference formula to help explain protein evolution. *Science.* 185:862-864, 1974.

EXAMPLE 1

Identification of Sources of Antibodies Suitable for HIV Immunotherapy

Despite progress in therapy of HIV infection, development of effective immunotherapies and vaccines for HIV remains an urgent need. Drugs like azidothymidine and retroviral protease inhibitors reduce viral burden. However, viral variants resistant to the drugs can develop, drug withdrawal can result in reestablishment of infection, and there are significant side effects. Recently, consensus has developed that both effector arms of the adaptive immune response, i.e., Abs and cytolytic T cells, are important in achieving protection against HIV-1 (1,2). Cytotoxic T cell responses correspond temporally with reduced viral burden in HIV-infected subjects. However, in vaccination strategies relying on cytolytic T cell responses, escape variants of HIV have been noted to develop (3,4). Cytolytic T cells lyse infected host cells—they do not inactivate cell-free virions and thus do not offer the possibility of sterilizing immunity. That the humoral immune system can protect against HIV is indicated by the identification of monoclonal neutralizing Abs that serve as entry inhibitors and control infection in the SHIV macaque model, e.g., Ab b12 directed against the CD4 binding site (CD4bs) of gp120, Ab 2G12 directed against a mannose-dependent epitope of gp120 and Ab 2F5 directed against gp41 (5-7). These Abs neutralize many but not all HIV-1 strains, prompting their use as cocktails in animal protection experiments (8).

Figure 4:
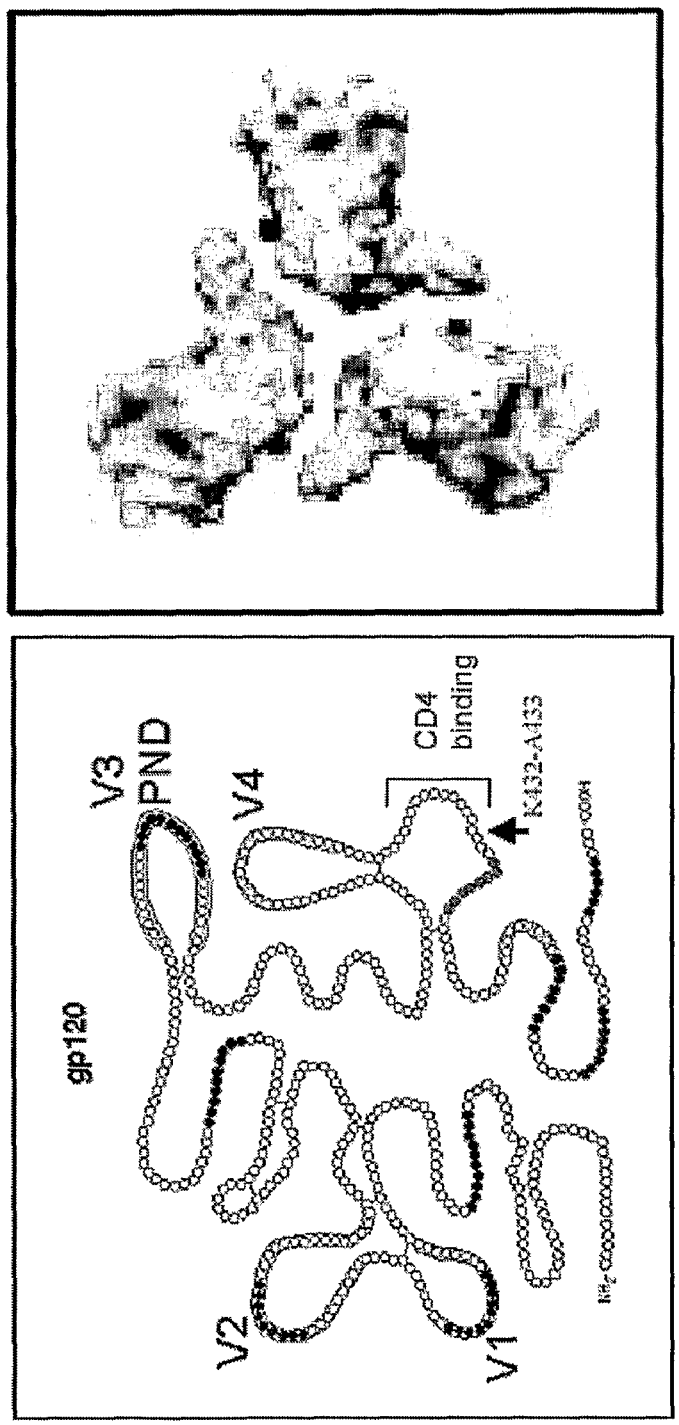
FIG. 4: gp120 domain structure and model of gp120 trimer. Determinant 421-436 is highlighted as an Ab target. From Kwong, P. D. et al., *J. Virol.* 74(4):1961-72, 2000.

Consideration of the Ab responses in HIV-infected subjects is instructive for development of HIV immunotherapeutic strategies. Proteolytic cleavage of the gp160 precursor at Arg511-Ala512 by a host cell protease produces gp120 and the integral membrane protein gp41. gp120 is expressed as a non-covalent trimer on the viral surface (FIG. 4). It's binding, to host cell CD4 receptors, followed by engagement of the chemokine coreceptor, initiates infection. In most HIV infected individuals, the Ab responses are ineffectual in controlling the infection. This is because of various immune diversionary techniques deployed by the virus. Immunodominant epitopes of the env proteins are also its most mutable regions. Most Abs to gp120 in infected individuals or produced by immunization with monomer gp120 are directed to a linear determinants in the V3 loop, the so-called principal neutralizing determinant (9,10). Anti-V3 Abs are usually strain-specific, i.e., they do not neutralize HIV-1 strains with altered V3 sequence developed in the course of infection or divergent strains from different geographical locations. Additionally, gp120 can undergo conformational changes upon interaction with host cell CD4 receptors/chemokine coreceptors. Several studies have described Abs that recognize neoepitopes induced after gp120 binds CD4 [e.g., 11]. A different class of Abs directed to the more conserved residues implicated in CCR5 binding may express broader neutralizing activity (12).

Insights to CD4-gp120 complexation have come from: (α) the X-ray structure of a ternary complex of truncated gp120 complexed with CD4 and the Fab fragment of a neutralizing Ab (clone 17b) (FIG. 5A), and (b) site directed mutagenesis in the relevant segments of gp120 (13-16). The CD5 binding site (CD4bs) is a discontinuous determinant composed of amino acids located in the 2nd, 3rd and 4th conserved segments, i.e., residues 256, 257, 368-370, 421-427 and 457. Abs to the CD4bs are infrequent in infected individuals, but they are sometimes elicited by immunization with gp120 (17,18). The CD4bs is susceptible to conformational changes when the gp120 trimer dissociates into monomers (19), which may account for lack of broad neutralization by some Abs to the CD4bs of the monomer. Several linear peptides containing residues 421-436 have been tested as immunogens to raise Abs (20-24). This determinant is largely but not fully conserved in different HIV strains. It is important to note that effective neutralization by an Ab that relies on steric hindrance mechanisms may require near-complete masking of the CD4bs. The greater the surface area of CD4bs occupied by the Ab paratope, the more the steric masking and the lesser the probability of viral escape due to CD4bs structural differences.

Abs raised by immunization with synthetic peptides containing the comparatively conserved residues 421-436 of gp120 (FIG. 5B) have been considered as possible HIV-1 neutralizing reagents. These Abs consistently recognize full-length gp120 and gp160 (20-24) and gp120 expressed on the surface of cells infected with diverse HIV isolates (21). Less consistent is their ability to inhibit HIV infection (20,21). Some of these Abs inhibit binding of gp120 by soluble CD4 but not by CD4 expressed on the cell surface (22,23). Variations in Ab neutralization activities may be due to fine differences in contacts between the Ab paratope and the CD4bs as discussed in the preceding paragraph. Such differences are not at all unlikely because the small peptide immunogens could assume varying conformations depending on their microenvironment, including contacts with carrier proteins). In our own studies, we noted marked carrier protein effects on the reactivity of Abs to synthetic gp120(421-436) with full-length gp120 (24). Moreover, although the overall structure of the CD4bs is sufficiently preserved to ensure binding to CD4, the reactivity of Abs with different HIV-1 strains can be influenced by sequence polymorphisms within and outside the CD4bs.

In addition to entry inhibition mechanisms, anti-HIV-1 Abs may interfere with viral replication and packaging if the Abs enter infected cells. Binding of gp120 by intracellular calmodulin is necessary for viral propagation, as revealed by the effect of calmodulin antagonists (25). Asp180 located between the V1 and V2 regions of gp120 is critical for viral replication (26). Certain full-length Abs are described to traverse the cell membrane. Because of their small size, engineered fragments of anti-HIV-1 Abs may enter cells more readily than full-length Abs.

Lupus and HIV may be related reciprocally. Several papers have commented on rare diagnosis of HIV infection in lupus patients (27-32). In the U.S. one report estimates the expected number of cases coexistent lupus and HIV-1 infection to be 400, but only 20 have been encountered (27). Interpretation of the relationship between lupus and HIV is complicated by certain common clinical and serological features of the two diseases (33). Similarly, the demographic and behavioral patterns of lupus patients may contribute to a lesser incidence of HIV (lupus occurs mainly in women; i.v. drug use and unsafe sexual habits in lupus patients were not strictly monitored but some effort has been made to take these factors into account in the published studies, refs 27-32). Alleviating these uncertainties is the fact that there are no known lupus patients who contracted HIV infection due to blood transfusion between 1978 and 1983 prior to institution of blood screening procedures [lupus patients receive transfusions, for example, following hemolytic episodes] (28). This suggests the existence of a specific resistance factor in lupus patients. Clinical amelioration of lupus following HIV infection is a well-accepted phenomenon (29-31). Similar results are reported in a mouse model of lupus exposed to retroviral infection (34).

Alterations in cell mediated immune responses in lupus are described, but no simple relationship of these changes with susceptibility to HIV infection has been seen. CD4+ cells are somewhat decreased and CD8+ cells are increased in lupus patients (35). CD4+ cells are hosts for HIV, and HIV-specific CD8+ cells have been implicated in fulfilling a protective role in HIV-infected individuals. No information is available about the presence of HIV-specific CD8+ cells in uninfected lupus patients. Enhanced production of Abs, a hallmark of lupus, is a potential resistance factor. Importantly, polyclonal Abs capable of binding gp120 are described both in lupus patients and mouse models of lupus (13,14). As noted previously, a critical factor influencing HIV neutralization is the epitope specificity. Lupus Abs display an epitope specificity distinct from the anti-gp120 HIV Abs found in HIV-infected individuals. The former recognize linear peptide composed of residues 421-436 (36,37). As this determinant is important in gp120 binding to CD4, the Abs can interfere with HIV entry into host cells.

Based on these considerations, we explored the lupus repertoire as a source of Abs suitable for HIV immunotherapy.

REFERENCES

1. Devico, A. L., Fouts, T. R., Shata, M. T., Kamin-Lewis, R., Lewis, G. K. and Hone, D. M. Development of an oral prime-boost strategy to elicit broadly neutralizing antibodies against HIV-1. *Vaccine*. 20:1968-1974, 2002.
2. Moore, J. P., Parren, P. W. and Burton, D. R. Genetic subtypes, humoral immunity, and human immunodeficiency virus type 1 vaccine development. *J Virol*. 75:5721-5729, 2001.
3. Altfeld, M., Allen, T. M., Yu, X. G., Johnston, M. N., Agrawal, D., Korber, B. T., Montefiori, D. C., O'Connor, D. H., Davis, B. T., Lee, P. K., Maier, E. L., Harlow, J., Goulder, P. J., Brander, C., Rosenberg, E. S. and Walker, B. D. HIV-1 superinfection despite broad CD8+ T-cell responses containing replication of the primary virus. *Nature*. 420:434-439, 2002.
4. Barouch, D. H., Kunstman, J., Kuroda, M. J., Schmitz, J. E., Santra, S., Peyerl, F. W., Krivulka, G. R., Beaudry, K., Lifton, M. A., Gorgone, D. A., Montefiori, D. C., Lewis, M. G., Wolinsky, S. M. and Letvin, N. L. Eventual AIDS vaccine failure in a rhesus monkey by viral escape from cytotoxic T lymphocytes. *Nature*. 415:335-339, 2002.
5. Burton, D. R., Pyati, J., Koduri, R., Sharp, S. J., Thornton, G. B., Parren, P. W., Sawyer, L. S., Hendry, R. M., Dunlop, N. and Nara, P. L. Efficient neutralization of primary isolates of HIV-1 by a recombinant human monoclonal antibody. *Science*. 266:1024-1027, 1994.
6. Stiegler, G., Armbruster, C., Vcelar, B., Stoiber, H., Kunert, R., Michael, N. L., Jagodzinski, L. L., Ammann, C., Jager, W., Jacobson, J., Vetter, N. and Katinger, H. Antiviral activity of the neutralizing antibodies 2F5 and 2G12 in asymptomatic HIV-1-infected humans: a phase I evaluation. *AIDS*. 16:2019-2025, 2002.
7. Stiegler, G., Kunert, R., Purtscher, M., Wolbank, S., Voglauer, R., Steindl, F. and Katinger, H. A potent cross-clade neutralizing human monoclonal antibody against a novel epitope on gp41 of human immunodeficiency virus type 1. *ARDS Res Hum Retroviruses*. 17:1757-1765, 2001.
8. Mascola, J. R. Passive transfer studies to elucidate the role of antibody-mediated protection against HIV-1. *Vaccine*. 20:1922-1925,2002.
9. Gorny, M. K., Xu, J. Y., Karwowska, S., Buchbinder, A. and Zolla-Pazner, S. Repertoire of neutralizing human monoclonal antibodies specific for the V3 domain of HIV-1 gp120. *J. Immunol*. 150:635-643, 1993.
10. Profy, A. T., Salinas, P. A., Eckler, L. I., Dunlop, N. M., Nara, P. L. and Putney, S. D. Epitopes recognized by the neutralizing antibodies of an HIV-1-infected individual. *J. Immunol*. 144:4641-4647, 1990.
11. Gershoni, J. M., Denisova, G., Raviv, D., Smorodinsky, N. I. and Buyaner, D. HIV binding to its receptor creates specific epitopes for the CD4/gp120 complex. *FASEB J*. 7:1185-1187, 1993.

12. Sharon, M., Kessler, N., Levy, R., Zolla-Pazner, S., Gorlach, M. and Anglister, J. Alternative conformations of HIV-1 V3 loops mimic beta hairpins in chemokines, suggesting a mechanism for coreceptor selectivity. *Structure* 11:225-236, 2003.

13. Olshevesky, T. J., Helseth, E., Furman, C., Li, J., Haseltine, W. and Sodroski, J. Identification of individual human immunodeficiency virus type 1 gp120 amino acids important for CD4 receptor binding. *J Virol.* 64:5701-5707, 1990.

14. Thali, M., Olshevsky, U., Furman, C., Gabuzda, D., Posner, M. and Sodroski, J. Characterization of a discontinuous human immunodeficiency virus type 1 gp120 epitope recognized by a broadly reactive neutralizing human monoclonal antibody. *J Virol.* 65:6188-6193, 1991.

15. Thali, M., Furman, C., Ho, D., Robinson, J., Tilley, S., Pinter, A. and Sodroski, J. Discontinuous, conserved neutralization epitopes overlapping the CD4-binding region of human immunodeficiency virus type 1 gp120 envelope glycoprotein. *J Virol.* 66:5635-5641, 1992.

16. Kwong, P. D., Wyatt, R., Robinson, J., Sweet, R. W., Sodroski, J. and Hendrickson, W. A. Structure of an HIV gp120 envelope glycoprotein in complex with the CD4 receptor and a neutralizing human antibody. *Nature.* 393: 648-659, 1998.

17. He, Y., Honnen, W. J., Krachmarov, C. P., Burkhart, M., Kayman, S.C., Corvalan, J. and Pinter, A. Efficient isolation of novel human monoclonal antibodies with neutralizing activity against HIV-1 from transgenic mice expressing human Ig loci. *J Immunol.* 169:595-605, 2002.

18. Lee, S. A., Orque, R., Escarpe, P. A., Peterson, M. L., Good, J. W., Zaharias, E. M., Berman, P. W., Sheppard, H. W. and Shibata, R. Vaccine-induced antibodies to the native, oligomeric envelope glycoproteins of primary HIV-1 isolates. *Vaccine.* 20:563-576, 2001.

19. Kwong, P. D., Doyle, M. L., Casper, D. J., Cicala, C., Leavitt, S. A., Majeed, S., Steenbeke, T. D., Venturi, M., Chaiken, I., Fung, M., Katinger, H., Parren, P. W., Robinson, J., Van Ryk, D., Wang, L., Burton, D. R., Freire, E., Wyatt, R., Sodroski, J., Hendrickson, W. A. and Arthos, J. HIV-1 evades antibody-mediated neutralization through conformational masking of receptor-binding sites. *Nature.* 420:678-682, 2002.

20. Neurath, A. R., Strick, N. and Lee, E. S. Y. B cell epitope mapping of human immunodeficiency virus envelope glycoproteins with long (19- to 36-residue) synthetic peptides. *J Gen Virol.* 71:85-95, 1990.

21. Morrow, W. J., Williams, W. M., Whalley, A. S., Ryskamp, T., Newman, R., Kang, C. Y., Chamat, S., Kohler, H. and Kieber-Emmons, T. Synthetic peptides from a conserved region of gp120 induce broadly reactive anti-HIV responses. *Immunol.* 75:557-564, 1992.

22. Clerget-Raslain, B., Benjouad, B., Van Rietschoten, J., Montagnier, L., Rochat, H. and Bahraoui, E. Specificity of anti-peptide antibodies elicited against synthetic peptides mimicking conserved regions of HIV 1 envelope glycoprotein. *Res Virol.* 142:423-438, 1991.

23. Ardman, B., Kowalski, M., Bristol, J., Haseltine, W. and Sodroski, J. Effects on CD4 binding of anti-peptide sera to the fourth and fifth conserved domains of HIV-1 gp120. *J Acquir Immune Defic Syndr.* 3:206-214, 1990.

24. Karle, S., Nishiyama, Y., Zhou, Y.-X., Luo, J., Planque, S., Hanson, C. and Paul, S. Carrier-dependent specificity of antibodies to a conserved peptide determinant of gp120. *Vaccine.* 21:1213-1218, 2003.

25. Srinivas, R. V., Bernstein, H., Oliver, C. and Compans, R. W. Calmodulin antagonists inhibit HIV-1 induced cell fusion but not virus replication. *AIDS Res Hum Retroviruses.* 108:1489-1496, 1994.

26. Wang, W. K., Essex, M. and Lee, T. H. The highly conserved aspartic acid residue between hypervariable regions 1 and 2 of human immunodeficiency virus type 1 gp120 is important for early stages of virus replication. *J Virol.* 69:538-542, 1995.

27. Barthel, H. R. and Wallace D. J. False positive human immunodeficiency virus testing in patients with lupus erythematosus. *Semin Arthritis Rheum.* 23:1-7, 1993.

28. Wallace, D. J. Lupus, acquired immunodeficiency syndrome and antimalarial agents. *Arthritis Rheum.* 34:372-373, 1991.

29. Daikh, B. E. and Holyst, M. M. Lupus-specific autoantibodies in concomitant human immunodeficiency virus and systemic lupus erythematosus: case report and literature review. *Semin Arthrisis Rheum.* 30:418-425, 2001.

30. Chang, B. G., Markowitz, G. S., Seshan, S. V., Seigle, R. L. and D'Agati, V. D. Renal manifestations of concurrent systemic lupus erythematosus and HIV infection. *Am J Kidney Dis.* 33:441-449, 1999.

31. Palacios, R., Santos, J., Valdivielso, P. and Marquez, M. Human immunodeficiency virus infection and systemic lupus crythematosus. An unusual case and a review of the literature. *Lupus.* 11:60-63, 2002.

32. Sekigawa, I., Lee, S., Kaneko, H., Iida, N., Hashimoto, H., Hirose, S. and Kaneko Y. The possible role of interleulcin-16 in the low incidence of HIV infection in patients with systemic lupus erythematosus. *Lupus.* 9:155-156, 2000.

33. Reveille, J. D. The changing spectrum of rheumatic disease in human immunodeficiency virus infection. *Semin Arthritis Rheum.* 30:147-166, 2000.

34. Mittleman, B. B., Morse, H. C. 3rd, Payne, S. M., Shearer, G. M. and Mozes, E. Amelioration of experimental systemic lupus erythematosus (SLE) by retrovirus infection. *J Clin Immunol.* 16:230-236, 1996.

35. Matsushita, M., Hayashi, T., Ando, S., Sekigawa, L., Iida, N., Hashimoto, H. and Hirose, S. Changes of CD4/CD8 ratio and interleukin-16 in systemic lupus erythematosus. *Clin Rheumatol.* 19:270-274, 2000.

36. Bermas, B. L., Petri, M., Berzofsky, J. A., Waisman, A., Shearer, G. M. and Mozes, E. Binding of glycoprotein120 and peptides from the HIV-1 envelope by autoantibodies in mice with experimentally induced systemic lupus erythematosus and in patients with the disease. *AIDS Res Hum Retroviruses.* 10:1071-1077, 1994.

37. Zhou, Y. X., Karle, S., Taguchi, H., Planque, S., Nishiyama, Y. and Paul, S. Prospects for immunotherapeutic proteolytic antibodies. *J Immunol Methods.* 269:257-268, 2002.

EXAMPLE 2

Recombinant Antibodies to gp120 from Autoimmune Patients

Renewable and homogeneous sources of well-characterized Abs are needed for passive immunotherapeutic applications. Traditional methods to clone Abs from humans consist of immortalizing lymphocytes derived from peripheral blood (or lymphoid tissues obtained by surgery), for example by transformation with Epstein Barr virus followed by fusion with a myeloma cell lines. The resultant hybridoma cell lines are screened for production of the desired Abs, for example by measuring the binding by ELISA.

Methods are also available to clone the expressed V domain repertoire of Abs in the form of libraries displayed on a suitable surface. The Ab fragments can be cloned as single chain Fv fragments (FIG. 6) or the light chain (L chain) subunits. Fv constructs usually reproduce faithfully the binding activity of full-length IgG Abs (e.g., 1). Previous reports have documented the antigen binding activity of L chain subunit independent of its H chain partner, albeit at reduced strengths compared to native Abs (2,3). The V domains of the Fv fragments are usually linked by S-S bonds or by peptide linkers. Cloning of Fv repertoires is usually accomplished by recovering MnRNA from lymphocytes and amplification by the reverse transcriptase-polymerase chain reaction. Similar procedures can be employed to clone the V domains of individual Abs produced by hybridoma cells. Mixtures of primers are employed to capture as large a proportion of the expressed repertoire as possible (e.g., 4). The primers anneal to comparatively conserved FR1 and FR4 nucleotide stretches located at the 5' and 3' ends of the V domains, respectively, allowing amplification of V domains belonging diverse V gene families. To obtain expressible Fv constructs, the VL and VH domains are cloned into a suitable vector containing a short flexible peptide and an inducible promoter. Transformation of bacteria with this vector followed by induction of the recombinant protein (e.g., using IPTG if the vector contains the lac operon) allows production of the desired Fv repertoire. Several molecular engineering maneuvers have enhanced the practical utility of this system. Including a leader peptide at the N terminus permits secretion of the Ab fragments into the bacterial periplasm, which helps avoid denaturation problems attendant to formation of intracellular inclusion bodies. Peptide tags such as the his6 tag are incorporated into the protein to enable rapid purification by metal affinity chromatography. The length and constitution of the peptide linker is an important variable in ensuring the appropriate intramolecular VL-VH interactions. With certain linkers, intermolecular VL-VH pairing can occur, resulting in formation of Fv aggregates (FIG. 6). The V domains can also be expressed in the form of Fab fragments containing full-length light chains linked by a disulfide bond to the VH-CH1 fragment of the heavy chain. The antigen binding activities of Fv and Fab constructs can approach those of full-length Abs, but loss of affinity due to the absent native Ab structure is sometime observed.

Once Ab repertoires cloned in bacteria are available, the next task is to isolate the minority of individual Abs with the desired antigen recognition characteristics. This can be accomplished using display technologies (4). Vectors permitting display of recombinant proteins on the surfaces of phages, retroviruses, bacteria and yeast have been developed. For example, fusion proteins composed of Ab fragments linked to a phage coat protein are expressed from phagemid or phage vectors in bacteria. Replication-incompetent helper phages are then added, allowing packaging of recombinant phages with functional Abs displayed on their surface. M13 filamentous phages are commonly used for this purpose, with the coat protein p3 or p8 located at the C terminal end of the Ab fusion protein. The packaged phages contain single stranded DNA encoding the Ab fusion protein. Fractionation of phages based on binding of the displayed Abs to inmmobilized antigen yields, therefore, the VL/VH genes of Abs with the desired specificity. As in routine affinity chromatography, phage binding can be conducted under conditions of increasing stringency to yield Abs with progressively increasing affinity. Phagemid vectors are useful because a codon at the junction of the Ab and phage coat protein genes is read as a sense codon by bacteria employed to package phages and as a stop codon by bacteria employed to obtain soluble Ab fragments free of the phage coat protein sequence.

Figure 7:
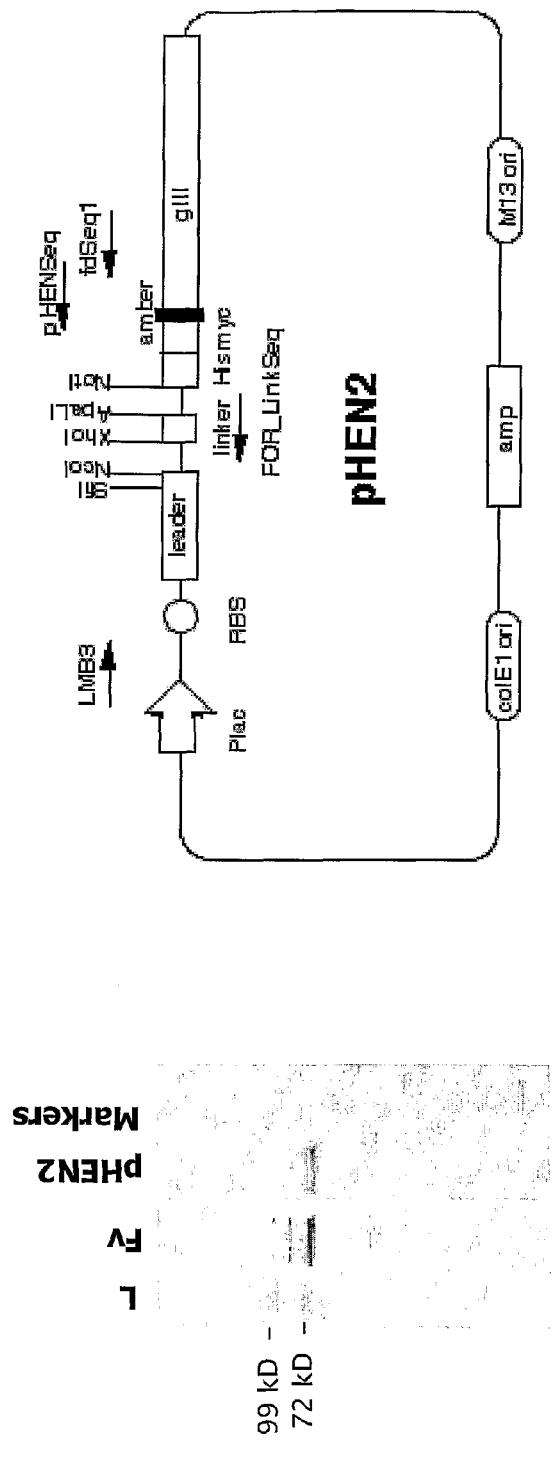
FIG. 7: Characteristics human lupus Fv and light chain libraries cloned in phagemid vector pHEN2 and pCT5his6, respectively. PBL, peripheral blood leukocytes. Insert length and diversity (% clones with unique sequences) determined by dideoxynucleotide sequencing of 10 and 9 randomly picked Fv and light chain clones, respectively. Library size is the total number of clones recovered following electroporation of the DNA into bacteria. Expression levels determined by dot-blots for the c-myc tag using periplasmic extracts. Bottom left, Anti-c-myc stained blot of SDS-gels of SDS (2%) extracts of lupus Fv phages, light chain phages and control phages packaged from pHEN2 harboring bacteria (12 pmol). The fusion protein and its breakdown products are visible as an anomalously migrating 99kD and 72-90 kD bands. pHEN2 phages show a 72 kD fusion protein (p3 expressing a 23 amino acid peptide at its N terminus). For methods, see Paul et al. *J. Biol. Chem.* 276:28314-28320, 2001.

Lupus anti-gp120 antibody fragments. We used the foregoing technologies to isolate anti-gp120 Ab fragments from lupus patients. We prepared the following phage displayed libraries (FIG. 7; ref 5): (a) human lupus L chains (from 3 patients) cloned in pCANTAB5his6 vector; and (b) human lupus single chain Fv constructs (from 2 patients) in pHEN2 (vector kindly provided by Center for Protein Engineering, MRC, England; patent WO9201047-A, GenBank accession 1926701). The Fv library was cloned as VL-linker-VH [linker: SS(GGGGS)2GGSA)] constructs. Following hypotonic lysis of erythrocytes in peripheral blood leukocytes (from 100 ml blood), total RNA was isolated, a cDNA copy prepared using forward primers, and the cDNA for full-length L chains and the VH, Vκ and Vλ domains was prepared by PCR (corresponding to residues 1-214; 1-123; 1-107; and, 1-107, respectively; Kabat numbering). Primers used were:

```
(a) Human full-length L chain:
V_LK back (Sfi I site underlined)-
SEQ ID NO 7:
GTCCTCGCAACTGCGGCCCAGCCGGCCATGGCCGACATCCAGATGACCCAGTCTCC,
SEQ ID NO 8:
GTCCTCGCAACTGCGGCCCAGCCGGCCATGGCCGATGTTGTGATGACTCAGTCTCC,
SEQ ID NO 9:
GTCCTCGCAACTGCGGCCCAGCCGGCCATGGCCGAAATTGTGTTGACGCAGTCTCC,
SEQ ID NO 10:
GTCCTCGCAACTGCGGCCCAGCCGGCCATGGCCGACATCGTGATGACCCAGTCTCC,
SEQ ID NO 11:
GTCCTCGCAACTGCGGCCCAGCCGGCCATGGCCGAAACGACACTCACGCAGTCTCC,
SEQ ID NO 12:
GTCCTCGCAACTGCGGCCCAGCCGGCCATGGCCGAAATTGTGCTGACTCAGTCTCC;
CK forward (Not I site underlined): SEQ ID NO: 13:
CCATCCTGCGGCCGCACACTCTCCCCTGTTGAAGCTCTT;

(b) Human single chain Fv:
V_LK back- see back primers, full-length L chain;
V_LK forward (Xho I site underlined) -
SEQ ID NO: 14:GCCTGAACCGCCTCCACCACTCGAGCGTTTGATTTCCACCTTGGTCCC,
SEQ ID NO: 15:
GCCTGAACCGCCTCCACCACTCGAGCGTTTGATCTCCAGCTTGGTCCC,
SEQ ID NO: 16:
GCCTGAACCGCCTCCACCACTCGAGCGTTTGATATCCACTTTGGTCCC,
SEQ ID NO: 17:
GCCTGAACCGCCTCCACCACTCGAGCGTTTGATCTCCACCTTGGTCCC,
```

-continued

SEQ ID NO: 18:
GCCTGAACCGCCTCCACCACTCGAGCGTTTAATCTCCAGTCGTGTCCC;

V_Lλ back (Sfi I site underlined) -
SEQ ID NO: 19:
GTCCTCGCAACTGCGGCCCAGCCGGCCATGGCCCAGTCTGTGTTGACGCAGCCGCC,
SEQ ID NO: 20:
GTCCTCGCAACTGCGGCCCAGCCGGCCATGGCCCAGTCTGCCCTGACTCAGCCTGC,
SEQ ID NO: 21:
GTCCTCGCAACTGCGGCCCAGCCGGCCATGGCCTCCTATGTGCTGACTCAGCCACC,
SEQ ID NO: 22:
GTCCTCGCAACTGCGGCCCAGCCGGCCATGGCCTCTTCTGAGCTGACTCAGGACCC,
SEQ ID NO: 23:
GTCCTCGCAACTGCGGCCCAGCCGGCCATGGCCCACGTTATACTGACTCAACCGCC,
SEQ ID NO: 24:
GTCCTCGCAACTGCGGCCCAGCCGGCCATGGCCCAGGCTGTGCTCACTCAGCCGTC,
SEQ ID NO: 25:
GTCCTCGCAACTGCGGCCCAGCCGGCCATGGCCAATTTTATGCTGACTCAGCCCCA;

V_Lλ forward (Xho I underlined) -
SEQ ID NO: 26:
GCCTGAACCGCCTCCACCACTCGAGCCTAGGACGGTGACCTTCGTCCC,
SEQ ID NO: 27:
GCCTGAACCGCCTCCACCACTCGAGCCTAGGACGGTCAGCTTGGT CCC,
SEQ ID NO: 28:
GCCTGAACCGCCTCCACCACTCGAGCCTAAAACGGTGAGCTGGGTCCC;
C_Lλ forward SEQ ID NO: 29:- TGAAGATTCTGTAGGGGCCACTGTCTT;

V_H back (ApaL site underlined) -
SEQ ID NO: 30: CATGACCACAGTGCACTTCAGGTGCAGCTGGTGCAGTCTGG,
SEQ ID NO: 31: CATGACCACAGTGCACTTCAGGTCAACTTAAGGGAGTCTGG,
SEQ ID NO: 32: CATGACCACAGTGCACTTGAGGTGCAGCTGGTGGAGTCTGG,
SEQ ID NO: 33: CATGACCACAGTGCACTTCAGGTGCAGCTGCAGGAGTCGGG,
SEQ ID NO: 34: CATGACCACAGTGCACTTCAGGTGCAGCTGTTGCAGTCTGC,
SEQ ID NO: 35: CATGACCACAGTGCACTTCAGGTACAGCTGCAGCAGTCAGG;

V_H forward (Not I site underlined) -
SEQ ID NO: 36: GAGTCATTCTGCGGCCGCGGGGAAGACSGATGGGCCCTTGGT,
SEQ ID NO: 37: GAGTCATTCTGCGGCCGCGGGGAAAAGGGTTGGGGCGGATGC;

Cloning of human Fv library in pHEN2 was by a two-step procedure—VH cDNA insertion via the ApaLI/NotI sites, and VL cDNA insertion via the SfiI/XhoI sites. Library sizes were—human L chain, 1.2×10$^6$; human Fv, 1.4×10$^7$. Randomly picked clones (at least five from each library) were sequenced by the dideoxy nucleotide sequencing method; 100 and 60% of the clones, respectively, contained full-length, stop codon-free, non-identical sequences.

Two types of phage selections were carried out using the lupus libraries as follows: binding of Fv phages to full-length gp120, and binding of L chain phages to synthetic gp120 (421-436). Phages displaying the Fv libraries were packaged from TG1 cells using M13K07 helper phages (10$^{13}$ particles) and selected by chromatography on recombinant gp120 (strain SF2: Austral Biologicals) immobilized on Affigel-10 (Biorad) via Lys sidechains (1 ml gel; 47 μg gp120/ml gel) using a pH 2.7 buffer for elution of bound phages (6). Similar procedures were applied to the L chain library except that the library had been preselected by binding to a phosphonate diester hapten (compound II in ref 5); this step enriches Abs with nucleophilic activity, see ref 5 discussion section). Phage selection was conducted by "panning" on synthetic gp120 (421-436) (KQIINMWQEVGKAMYA, corresponding to the consensus sequence of this determinant in clade B strains; 22). The peptide was immobilized Nunc Maxisorp tubes; 10 μg peptide), blocked with 5% BSA, incubated with phages for 1 h and unbound phages removed by washing with 10 mM sodium phosphate, 137 mM NaCl, and 2.7 mM KCl, pH 7.4 containing 0.05% Tween-20 (PBS-Tween). Bound phages were eluted with 0.1 M glycine-HCl, pH 2.7 and neutralized using 1 M Tris base. HB2151 cells were infected with the eluted phages, permitting expression of soluble Ab fragments.

Figure 8:
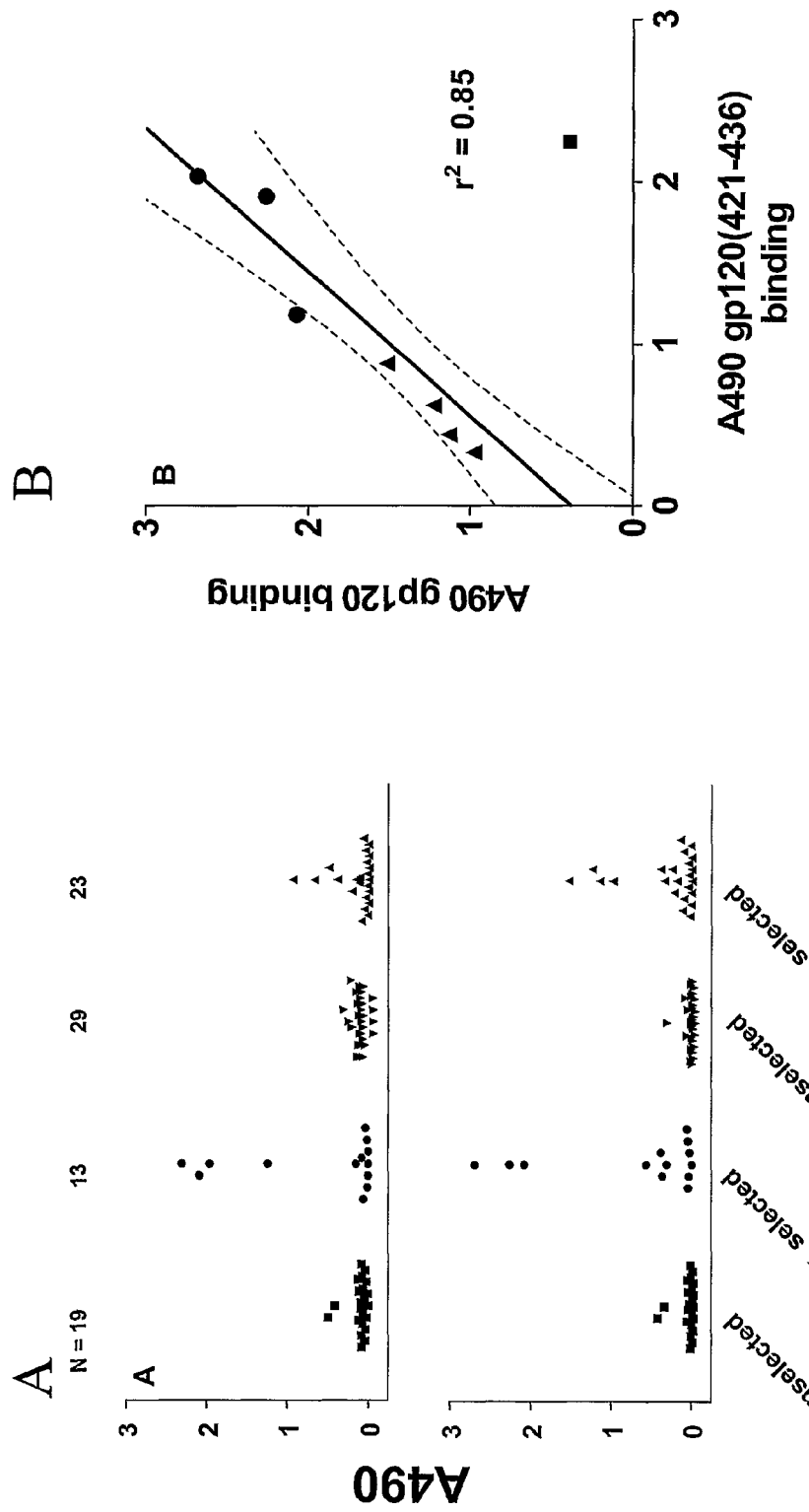
FIG. 8: Selection of phage anti-gp120 antibody fragments from lupus libraries (A); and, correlated binding of lupus antibody fragments to full-length gp120 and synthetic gp120 (421-436) (B). Shown are ELISA values for Fv and L chain clones isolated by prior binding of phage particles to immobilized gp120 and synthetic gp120, respectively (selected clones) or picked randomly from the unfractionated source libraries (unselected clones). N=number of independent clones. A, Top, Immobilized synthetic gp120(421-436)-BSA conjugate. A, bottom, Immobilized full-length gp120. B. Plotted are selected Fv and L chain clones displaying A490>0.3 in FIG. 1. Fv clones shown are: JL409, JL413, JL437 (♦) and JL427 (■). L chain clones are SK18, SK45, SK41, SK51 (▲). P=0.0004 for regression line (computed by excluding Fv JL427; $r^2$=0.24, P=0.15 with inclusion of this Fv). Data are corrected for binding by periplasmic extracts of bacteria harboring the vector without Ab insert [A490 0.10 and 0.14 for gp120(421-436) and gp120 binding, respectively]. Recombinant Ab expression determined for 10 clones was 1.9±0.5 (s.e.m.) mg/liter bacterial culture.

Soluble Ab fragments obtained by expressing selected phagemid DNA in HB2151 bacteria were screened for binding to gp120 and gp120(421-436) by ELISA. Immobilized Cys-gp120(421-436) conjugated to bovine serum albumin (BSA; 10 mol peptide/mol BSA; 230 ng peptide equivalents/well) or full-length monomer gp120 (100 ng/well, MN strain, Immunodiagnostics Inc.) were coated on Maxisorp 96-well microtiter plates (Nunc; 1 h) (6). The plates were blocked with 5% skim milk and incubated with Ab fragments in PBS-Tween containing 0.1% milk (1 h) in triplicate. Bound Ab fragments were detected using mouse anti-c-myc Ab (clone 9E10; 1:500 delipidated ascites) followed by peroxidase-conjugated goat anti-mouse IgG (1:1000; Fc specific, Sigma). Fifty four percent and 26% of selected Fv and L chain clones were bound by full-length gp120, respectively, and 31% and 17% were bound by gp120(421-436), respectively (FIG. 8A). Except in the case of one Fv clone, binding of the two antigens was highly correlated (FIG. 8B).

Figure 9:
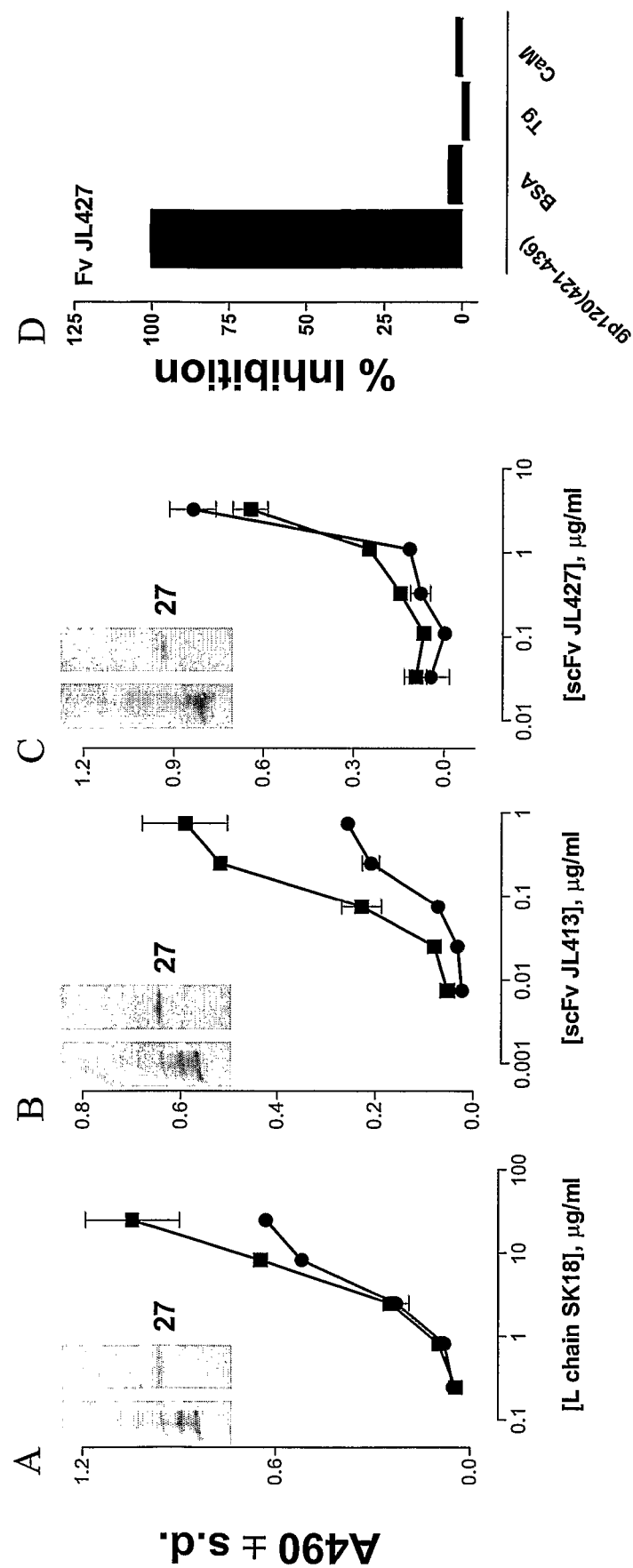
FIG. 9: Concentration-dependent binding of immobilized gp120(421-436) (■) and full-length monomer gp120 (▲) by lupus antibody fragments (A-C) and specificity of binding to immobilized gp120(421-436) (D). Ab fragments purified by metal affinity chromatography. In D, Fv JL427 (46 µg/ml) was assayed for binding in the presence of soluble gp120 (421-436), bovine serum albumin (BSA), thyroglobulin (Tg) and calmodulin (CaM) (1 µM). Insets, silver stained SDS-polyacrylamide electrophoresis gels (8-25%) showing 27 kD purified Ab fragments purified (right lane in each panel) and marker proteins (left lane; from top to bottom, 94, 67, 43, 30, 20, 14 kD; Pharmacia).

Two Fv clones (JL413, JL427) and one L chain clone (SK18) were characterized further. Periplasmic extracts were prepared following induction with isopropyl-β-D-thiogalactoside and recombinant proteins were purified by metal affinity chromatography to electrophoretic homogeneity (the Ab fragments contain a his$_6$ tag; ref 5). SDS-polyacrylamide electrophoresis was on 8-25% gels, with identity of the proteins confirmed by immunoblotting using anti-cmyc Ab as described previously (5) (the Ab fragments contain a ten residue c-myc peptide close to their C terminus). The electrophoretically pure Fv and L chains from these clones displayed concentration-dependent binding to gp120 and gp120 (421-436) (FIG. 9A-C). Competitive ELISA studies were conducted in which the recombinant Abs were pretreated with diluent or competitor proteins (1 μM; calmodulin, BSA, thyroglobulin; Sigma) for 1 h and then analyzed by ELISA for binding to gp120(421-435). No reactivity of Fv JL427 with proteins unrelated to gp120(421-436) was evident (FIG. 9D).

HIV neutralization assays using peripheral blood mononuclear cells (PBMC) hosts were carried out as described in (9) but with p24 quantification as the measure of infection.

TABLE 4

Characteristics of lupus antibody fragments deduced from V domain sequences.

|  | L chain SK-18 | Fv JL-413 | | Fv JL-427 | |
|---|---|---|---|---|---|
|  |  | VL | VH | VL | VH |
| Family | I | I | IV | I | V |
| Subgroup | I | I | II | I | III |
| Germline Counterpart | 02/012, Jk1 | L5, Jk4 | VH4-59, JH5 | V1-17, JL3 | VH3-48, JH6 |
| CDR length* |  |  |  |  |  |
| 1 | 11 | 11 | 5 | 13 | 5 |
| 2 | 7 | 7 | 16 | 7 | 17 |
| 3 | 9 | 7 | 5 | 11 | 9 |
| Mutations |  |  |  |  |  |
| R | 4 | 9 | 4 | 14 | 13 |
| S | 3 | 3 | 3 | 8 | 2 |
| R/S CDRs | 1/0 | 6/0 | 3/1 | 9/3 | 8/1 |
| R/S FRs | 3/3 | 3/3 | 1/2 | 5/5 | 5/1 |

R—Replacement mutations; S—Silent mutations. *, number of amino acids. Germline counterparts identified from www.ncbi.nlm.nih.gov/igblast. CDRs identified by comparison with Kabat database. Mutation counts restricted to 3' termini of V genes. FR1 residues 1-7 excluded because these are encoded by PCR back primers. Family and subgroup assignment from immuno.bme.nwu.edu/. cDNA sequences determined in the 5' and 3' directions were identical. Alignments with germline V and J genes suggested extensive diversification due to V-(D)-J recombination. For this reason, germline D genes were unassignable. Fv JL413 contained 20 and 17 deletions at the VH gene 3' end and J gene 5' end, respectively.

The Fv and L chain clones were sequenced by standard dideoxynucleotide sequencing methods (FIG. 10). Comparison of the cDNA sequences of Fv JL413 and Fv JL427 with their closest germline V gene counterparts revealed extensive replacement mutations in the regions contributed by the $V_L$ and $V_H$ genes (Table 4). The mutations tended to cluster in the complementarity determining regions (CDRs). The ratios of replacement to silent mutations in the six CDRs for each Fv clone was greater than for the framework regions (FRs), suggesting adaptive maturation of the V genes by somatic hypermutation processes (8). The $V_L$ domain of L chain clone SK18 contained 4 replacement mutations, with 1 replacement in the CDRs. Nonetheless, the replacement/silent mutation ratio for the CDRs remains greater than for FRs, as all of the silent mutations are located in the FRs.

Study of neutralization of HIV infection in T cell and macrophage cultures by Abs is established method to analyze their potential utility in immunotherapeutic applications. In the older literature, lab-adapted strains of HIV-1 such as strains IIIB and MN were commonly employed as the indicator strains in the assays. However, these strains utilize the CXR4 chemokine coreceptor along with CD receptors to gain entry into host cells, and are generally more readily neutralized by Abs than the CCR5 chemokine coreceptor primary HIV-1 isolates. Similarly, use of peripheral blood mononuclear cells (PBMCs) as the host cells is desirable compared to cell line hosts, as the former more accurately predict the infection process in vivo. Recently, single-cycle infectivity assays designed to measure the entry inhibiting effect of Abs have become available. These assays utilize replication-deficient virus pseudotypes expressing gp120 from defined virus strains and host cell lines expressing defined CD4 and chemokine receptors. While these assays have proved useful to determine the neutralizing effect of established anti-HIV Abs, it is not clear that they are suitable for screening of Abs with novel epitope specificities. In our studies, therefore, we employed primary HIV-1 isolates and PBMC hosts to study the neutralizing activity of recombinant Fv and L chains isolated from lupus patients.

The following primary isolates of HIV-1 were obtained from the NIH AIDS Research and Reference Reagent Program: ZA009 (coreceptor CCR5, clade C), BR004 (coreceptor CCR5, clade C), Ug046 (coreceptor CXCR4, clade D) and SF-162 (coreceptor CCR5, clade B). HIV-1 primary isolate strain 23135 (coreceptor not known, clade B) was from Dr. Sandra Levine (Univ Southern California). Each virus stock was titered in preliminary studies with each batch of donor PBMCs to determine the working dilution giving the optimum TCID50. The working dilution was adjusted to give p24 signal sufficient to be measured reproducibly in the linear range of the p24 assay after 4 days. The virus in RPMI was treated in quadruplicate with equal volumes of increasing concentrations (up to 50 µg/ml) of metal affinity-purified Fv or L chain in PBS (1 h; TCID50 for virus=100). Phytohemagglutinin-stimulated PBMCs from healthy human donors (0.25 million) were added to virus-Ab fragment mixtures and incubated for 3 days (37° C.), the cells washed twice with PBS and once with RPMI1640, incubated in fresh RPMI for 24 h, lysed with Triton X-100, and p24 in supernatants measured by an enzymeimmunoassay kit (Beckman Coulter p24 Assay Kit; linear range 50-3200 pg/ml). Negative controls included the virus (strain ZA009) treated with: (a) diluent, (b) metal affinity purified extract of bacteria harboring pHEN2 vector (processed identically as recombinant Ab preparations); (c) light chain clone GG63 and SK161 (11 µg/ml, ref 5); and (d) Fv clones JL610 and JL611 (2.5 µg/ml). IgG clone b12 was kindly provided by Dr. Dennis Burton as a reference Ab.

Figure 11:
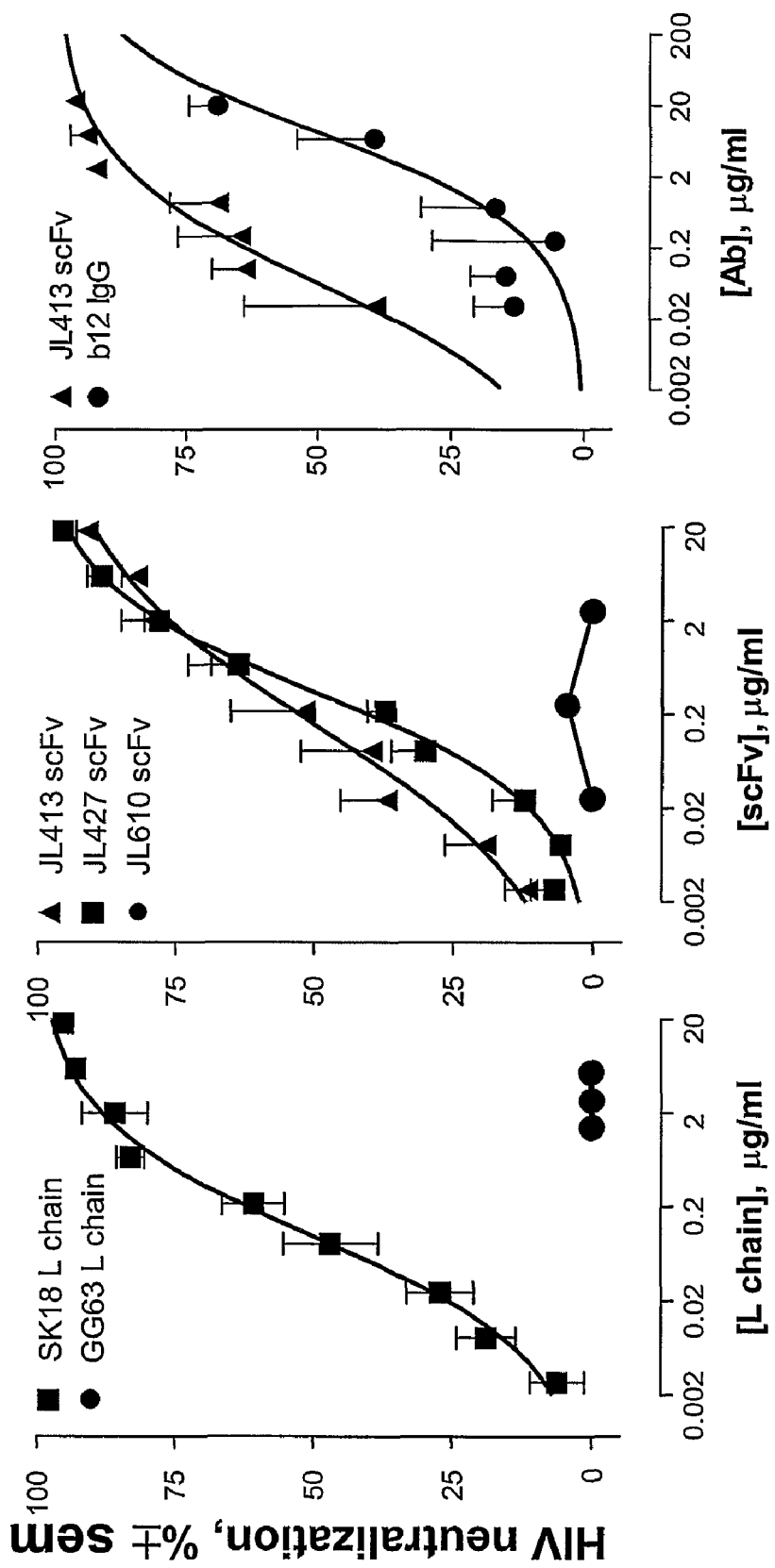
FIG. 11: Concentration-dependent HIV-1 neutralization by purified lupus antibody fragments. A & B, HIV-1 strain ZA009 (clade C). C, HIV-1 strain BR004 (clade C). Host cells: PBMCs. Values are percent of p24 concentrations in wells containing HIV treated with diluent instead of Abs (in PBS). Four culture replicates analyzed individually for p24 concentration (means, sem).

Progressively increasing neutralization of strain ZA009 by increasing concentrations of Fv JL413, Fv JL427 and L chain SK18 was observed (FIG. 11). In control studies, no loss of HIV infectivity (strain ZA009, clade C) was evident in the presence of identically purified irrelevant Fv and L chains (control Fv clone JL610 and L chain clone GG63 shown in FIG. 11; not shown, control Fv clone JL611, 2.5 µg/ml; control L chain clone SK161, 11 µg/ml) and the purified extract of bacteria harboring vector devoid of Ab inserts. At the aforementioned concentrations of the control clones, >75% neutralization of ZA009 strain was consistently observed in the presence of Fv JL413, Fv JL427 and L chain SK18.

PBMC viability determination following incubation with Fv JL413, Fv JL427 or L chain SK18 in the absence of HIV-1 (27 µg/ml, 72 h) was by staining with acridine orange (2 µg/ml) and ethidium bromide (1 µg/ml) followed by counting the viable cells (green fluorescence) using a hemocytometer and a UV microscope. Inhibition of infection was not due to a cytotoxic effect, as no loss of cell viability was observed following incubation with Ab fragments in the absence of HIV. PBMC viability after treatment with diluent, Fv JL413, Fv JL427 and L chain SK18 (Ab fragment concentration, 27 µg/ml) was 81.2±2.8%, 76.8±3.9%, 82.1±4.0% and 79.0±2.8%, respectively (150-200 cells. counted).

Dose-dependent neutralization of the primary HIV-1 isolates drawn from clades B, C and D by the purified Fv clones was observed (Table 2). Strains ZA009, SF-162 and BR004 utilize coreceptor CCR5, and clade D strain Ug046, coreceptor CXCR4. The L chain clone neutralized two of the three strains analyzed. Assays using independent preparations of the Ab fragments indicated reproducible neutralizing activity [strain ZA009, N=3, IC50 for L chain SK18 L chain, Fv JL413 and Fv JL427: 0.4 0.3, 0.2 0.1 and 0.3 0.1 (s.d.) µg/ml, respectively; strain Ug046, N=2, IC50 for L chain SK18 and Fv JL413: 11.6-13.5 and 2.1-5.5 µg/ml, respectively]. Side-by-side comparisons suggested that the neutralizing potency of Fv JL413 was comparable to IgG b12, a broadly neutralizing Ab to the CD4bs.

These observations indicate that the lupus Fv clones recognize the comparatively conserved gp120 determinant composed of residues 421-436. As the phage Fv clones were isolated by binding to full-length gp120, their ability to bind synthetic determinant 421-436 suggests this to be the major epitope recognized by lupus Abs. As the phage L chain clones were isolated by binding to synthetic gp120(421-436), their reactivity with full-length gp120 indicates the ability of the peptide to assume a conformation similar to the corresponding epitope in full-length gp120. The binding activity was specific for gp120 and the V domains of the Ab fragments contained extensive mutations typical of adaptive maturation. The observed HIV neutralizing properties of the Ab fragments may reflect a protective role against HIV infection. However, this point must be evaluated in larger groups of lupus patients to determine whether the Abs accumulate in, amounts sufficient to neutralize HIV and the extent to which combinatorial VL/VH domain pairing in the Fv library replicates the natural pairs found in intact Abs. Regardless of caveats concerning their functional role in lupus, the availability of homogeneous preparations of broadly neutralizing Abs is of value for their potential immunotherapeutic utility.

The Fv clones displayed cross-clade neutralization of primary HIV isolates dependent on R5 and X4 coreceptors. This profile is consistent with the comparatively conserved character of determinant 421-436 in diverse HIV-1 strains and the contribution by determinant 421-436 of key contact sites for host cell CD4 receptor binding. The percent frequency of the consensus amino acids in determinant 421-436 of 384 HIV-1 strains listed in the Los Alamos database is as follows (values in parentheses; all clade A, B, C, D, F, G, H, J, U, N and O as well as the CRF and CPZ classifications are included): Lys (91), Gln(99), Ile(92), Ile(65), Asn(86), Met(83), Trp(99), Gln(96), Glu(41), Val(87), Gly(97), Lys(42), Ala(95), Met (84), Tyr(99), Ala(98). The sequence polymnorphisms are located primarily at residues 429 (Glu) and 432 (Lys). Fine structural differences resulting from such polymorphisms could potentially impact Ab neutralizing activity. Assessing the extent to which the Ab neutralizes HIV-1 despite sequence polymorphisms requires additional studies. However, certain initial conclusions are available. The two Fv clones neutralized strains ZA009 and Ug046 despite the sequence difference at position 429 (Lys and Gly, respectively). Similarly, binding of the Ab fragments to synthetic determinant 421-436 from strain SF2 was generally correlated with binding to full-length gp120 from strain MN, despite the sequence difference at position 429 (Glu and Lys, respectively). Evidently, the Ab binding and neutralizing activities are maintained despite these differences.

The epitope-specificity of the Fv clones, i.e., recognition of the linear determinant 421-436 sets these clones apart from other monoclonal Abs that recognize discontinuous segments of the CD4bs. Variations in the HWV neutralizing activity of different Abs to the CD4bs were noted previously (e.g., ref). The fine specificity of the Abs is an important factor governing their neutralizing activity. In the present study, binding to synthetic determinant 421-436 was useful for initial identification of the Abs, but the extent of binding did not correlate fully with neutralization efficacy. For instance, L chain SK18 displayed low level binding compared to the 2 Fv clones, but all 3 Ab fragments neutralized HIV strains ZA009 and Ug046 with comparable potency (Table 2). Differences in strain-reactivity of the individual Ab fragments are also evident, e.g., neutralization of strains ZA009 and Ug046 but not strain 23135 by the L chain. Reports on Abs raised by experimental immunization with synthetic peptides also suggest the importance of Ab fine specificity. In one report, polyclonal neutralizing Abs were obtained by immunization with a synthetic peptide corresponding to residues 418-445 (11). In another report, monoclonal Abs raised by immunization with determinant 421-438 failed to neutralize HIV-1 despite binding to gp120 expressed on cells infected with HIV (12). The differing properties of these Abs may be explained by distinct conformations adopted by the short peptides use as immunogens (peptides can assume different conformations dependant on their microenvironment and differences in length). The Abs can be anticipated to neutralize HIV-1 only if they generate sufficient steric hindrance to interfere with the binding of CD4. Abs that establish sufficiently strong binding at key residues involved in gp120-CD4 binding should block the latter interaction even without occupying the entire CD4bs surface. In comparison, Abs that bind at CD4bs residues not directly involved in the interaction with CD4 leave open the possibility of virus attachment to the host cell receptor.

REFERENCES

1. Pantoliano, M. W., Bird, R. E., Johnson, S., Asel, E. D., Dodd, S. W., Wood, J. F. and Hardman, K. D. Conformational stability, folding, and ligand-binding affinity of single-chain Fv immunoglobulin fragments expressed in *Escherichia coli. Biochemistry.* 22:10117-10125, 1991.
2. Masat, L., Wabl, M. and Johnson, J. P. A simpler sort of antibody. *Proc Natl Acad Sci USA.* 91:893-896, 1994.
3. Sun, M., Li, L., Gao, Q. S. and Paul, S. Antigen recognition by an antibody light chain. *J Biol Chem.* 269:734-738, 1994.
4. Marks, J. D., Hoogenboom, H. R., Bonnert, T. P., McCafferty, J., Griffiths, A. D. and Winter, G. By-passing immunization. Human antibodies from V-gene libraries displayed on phage. *J Mol Biol.* 222:581-597, 1991.
5. Paul, S., Tramontano, A., Gololobov, G., Zhou, Y. X., Taguchi, H., Karle, S., Nishiyama, Y., Planque, S., and George, S. Phosphonate ester probes for proteolytic antibodies. *J Biol Chem.* 276:28314-28320, 2001.

6. Tyutyulkova, S., Gao, Q. S., Thompson, A., Rennard, A. and Paul, S. Efficient vasoactive intestinal polypeptide hydrolyzing autoantibody light chains selected by phage display. *Biochim Biophys Acta.* 1316:217-223, 1996.
7. Karle, S., Nishiyama, Y., Zhou, Y. X., Luo, J., Planque, S., Hanson, C. and Paul, S. Carrier-dependent specificity of antibodies to a conserved peptide determinant of gp120. *Vaccine.* 21:1213-121, 2003.
8. Nossal, G. J. B lymphocyte physiology: the beginning and the end. *Ciba Found Symp.* 204:220-230, 1997.
9. Karle, S., Planque, S., Nishiyama, Y., Taguchi, H., Zhou, Y. X., Salas, M., Lake, D., Thiagarajan, P., Arnett, F., Hanson, C. V. and Paul, S. Cross-clade HIV-1 neutralization by an antibody fragment from a lupus phage display library. *AIDS.* 18:329-331, 2004.
10. Lake, D. F., Kawamura, T., Tomiyama, T., Robinson, W. E., Matsumoto, Y., Masuho, Y. and Hersh, E. M. Generation and characterization of a human monoclonal antibody that neutralizes diverse HIV-1 isolates in vitro. *AIDS.* 6:17-24, 1992.
11. Neurath, R. A., Strick, N. and Lee, E. S. B cell epitope mapping of human immunodeficiency virus envelope glycoproteins with long (19- to 36-residue) synthetic peptides. *J Gen Virol.* 71:85-95, 1990.
12. Morrow, W. J., Williams, W. M., Whalley, A. S., Ryskamp, T., Newman, R., Kang, C. Y., Chamat, S., Kohler, H. and Kieber-Emmons, T. Synthetic peptides from a conserved region of gp120 induce broadly reactive anti-HIV responses. *Immunology.* 75:557-564, 1992.

EXAMPLE 3

Engineering Improved Anti-HIV-1 Antibodies

For the purpose of antigen binding, the V domains are thought to be the minimal flnctional units. Once anti-HIV Ab fragments with the correct specificity are obtained, they can be improved by standard Ab engineering methods. The feasibility of engineering therapeutic grade Abs is supported by the development of a human Fv construct against tumor necrosis factor using a phage library prepared from unimmunized human subjects. Recloned as full-length IgG, this construct has been recently approved for the treatment of rheumatoid arthritis (1).

Monitoring the level of antigen binding activity as described above is a useful way to determine improvements in the activity of the engineered Ab fragments. In addition, HIV neutralization tests are performed to confirm that the activity of the clones has been improved. This is important because the molecular manipulations may induce unintended changes in epitope specificity. Similarly, subtle changes in the properties of the Fv after recloning as full-length Abs cannot be excluded. Therefore, careful monitoring of the behavior of full-length IgG/IgM Abs containing the Fv V domains is carried out. Potential alterations in antigen recognition could occur due to the $V_L$-$V_H$ linker segment. Some Fv constructs tend to aggregate due to intermolecular interactions (this occurs when intramolecular $V_L$-$V_H$ pairing is disfavored). In such instances, changing the order of the $V_L$ and $V_H$ domains in the Fv construct can help relieve intramolecular constraints and restore the predicted behavior. The Fv expression method described here is a non-denaturing system. In the unlikely event that problems are encountered with correct folding or low expression levels, we can employ alternative expression systems, e.g., the baculovirus expression system.

We have optimized phage technology in our lab and have identified high affinity phage Abs to several antigens. Care is taken to minimize skewing library diversity due to bias in protein expression or growth rates, e.g. phage libraries are not propagated serially as far as possible. The number of selections is minimized by using alternative procedures such as affinity chromatography permitting single step recovery of low and high affinity binders as the elution pH is progressively reduced to elute the phages. The proportion of phages with full-size inserts often decreases at successive cycle of enrichment. Fv insert size is monitored between selection steps by PCR to ensure that full-length insert are maintained. Use of a novel hyperphage packaging system allows recovery of phages free of bald particles devoid of displayed Fv which are commonly seen in conventional helper phage packaging systems Domain linkage and expansion. The neutralizing potencies of the lupus Fv clones compare favorably with monovalent Fab fragments and bivalent IgG Abs proposed as candidates for HIV immunotherapy. A further gain in potency is realized by recloning the monovalent Fv clones as bivalent IgG. The IgG version of a monovalent Fab has previously been reported to displays 400-fold increased neutralized potency due to enhanced binding avidity (2). Decavalent expression of the monovalent Fv should increase the HIV-1 binding avidity further.

Another important factor is the pharmacokinetics of full-length Abs versus Fv and Fab fragments. Half-lives for Fv and Fab constructs are usually on the order of hours, whereas IgG and IgM Abs display half-lives ranging from weeks to days, respectively. Therefore, to achieve persistent neutralization of the antigen, the preferred reagents are the full-length Abs. On the other hand, the smaller Fv constructs may offer tissue penetration capabilities superior to full-length Abs. For example, Fv constructs intended for HIV immunotherapy may permeate tissue viral reservoirs more efficiently than the full-length Abs.

The constant domains bring to Abs certain effector functions, for example, the ability to fix complement, mediate Ab-dependent cellular cytotoxicity and bind Fc receptors expressed on antigen presenting cells. Moreover, recloning of the Fv as IgA Abs permits protection against HIV-1 in mucosal fluids, as IgA Abs can cross epithelial surfaces.

Full-length Abs are obtained from Fv constructs by recloning into mammalian cell expression vectors. The vectors contain cDNA encoding the constant domains of the desired Ab class and subclass (3). Fv recloning as IgG1 and IgM constructs is accomplished by standard methodology (4). The vectors are available commercially, for example, from Lonza. The vectors contain human Ab constant domains flanked by restriction sites for insertion of foreign V domains. $V_L$ and $V_N$ domain cDNA are amplified from pHEN2 plasmid DNA using back/forward primers containing appropriate restriction sites present in the vectors. The $V_L$ domain of the Fv is cloned into the vectors on the 5' side of the κ constant region, and the $V_H$ domain on the 5' side of the appropriate heavy chain domain (e.g., γ1, α and μ constant regions). The vectors contain have antibiotic resistance genes for selection. Stable transfectants are prepared in CHO cells or another mammalian cell line (Ab yield, 5-30 μg/ml). Purification of IgG, IgA and IgM is done using immobilized protein G, anti-IgA and anti-IgM Ab.

Increased avidity of HIV-1 binding can also be obtained by forming multimers of the Fv. For example, tetravalent Ab fragments are generated by placing a 33-amino acid self-aggregating peptide derived from the GNC4 protein at the C terminus of an Fv construct (reviewed in ref 5). The peptide associates noncovalently into a 4-helix bundle, permitting expression of multiple valencies by the homotetramer. As the overall binding strength for multivalent binding (binding avidity) is substantially greater than the sum of the binding strength for the individual combining sites, virtually irreversible binding can be obtained by these means. The linker methodology can also be applied to generate bispecific Abs, i.e., Abs comprised of two Fv components with differing antigenic specificity (5). In this instance, the goal is to target two distinct antigens, e.g., a bispecific construct directed to the transferrin receptor and CD3 is shown to direct CD3+ T cells to lyse cells expressing the transferrin receptor.

Domain linkage technologies can also be applied to prepare conjugates of Abs with toxins such as ricin and pseudomonas exotoxin to induce death of infected cells. The Ab component of the engineered construct lends specificity for individual target molecules. For example, the specificity of Ab-toxin conjugates for tumor associated antigens helped limit generalized negative effects of the toxin (6). Similarly, binding of an Ab conjugate of β-lactamase to tumor cells allows activation of a doxorubicin prodrug in the vicinity of the tumor cells (5).

Affinity maturation in vitro. As noted previously, the antigen binding affinity strength is a key determinant of the neutralization potency of Abs. Selective binding of antigens to the B cell receptor (surface Ab complexed to Igα and Igβ subunits) expressing the greatest binding affinity drives the proliferation of B cells. Thus, V domain mutations that enhance the binding affinity are selected, a process termed affinity maturation. This process is simulated in vitro as follows. Mutations are introduced into the CDRs using mutagenic primers and the mutant molecules are expressed on the surface of phages. Antigen binding is employed to fractionate phages with the greatest binding affinity. The process is repeated several times, with additional mutations introduced at each cycle followed by the phage separation by antigen binding. Antigen-specific Fv clones with binding affinity as great as $10^{10}$-$10^{11}$ M$^{-1}$ ($K_a$) have been obtained using as starting material the Fv repertoire expressed by unimmunized human donors. The 6 CDRs of the VL and VH domains contain about 100 amino acids. Study of Abs that are comprehensively mutated at these residues with each of the 20 natural amino acids is impractical because of the large size of the resultant mutant library (~$100^{20}$ clones). CDR3 of the VH domain is often chosen for introducing mutations, as antigen contacts at CDRH3 are thought to impart specificity to antigen-Ab interactions. Several groups have reported that optimizing the structure of the $V_H$ CDR3 improves the antigen binding properties (7-10). An example of improved HIV-1 recognition by this strategy follows.

$V_H$ CDR3 can be up to 23 residues in length. Each CDR3 residue is replaced by all possible 20 amino acids using a CDR walking mutagenesis procedure employed previously by other groups (7,8). As it is impractical to use phage libraries larger than ~$10^8$ clones (due to constraints imposed by phage solubility and transfection), mutagenesis is done in a stepwise fashion. For example, the 5 N-terminal CDR residues are initially randomized and the resultant phage library (library 1) is selected for binding to gp120 (or whole HIV) as described above. Then the next 5 CDR3 residues is randomized (library 2), followed again by antigen binding selection. This process is repeated until the entire CDR has been spanned. In this scheme, library 1 is composed of $6.4 \times 10^7$ clones, a number of clones that can be easily manipulated. At each subsequent step, a few selected clones with favorable properties (see screening procedure below) are identified addition mutagenesis. By this process, optimization of the gp120 binding and HIV-1 neutralizing properties is achieved.

Randomization of the $V_H$ CDR3 residues is done by the method described in ref 8, consisting of mutagenesis by overlap extension. Essentially two separate PCR amplifications are carried out, corresponding to amplification of the $V_H$ cDNA region in which no mutation is to be introduced and another amplification of the cDNA region to be mutated. In the latter PCR, mutagenic back primers are employed, containing all 4 bases at each position to be mutated. Once the two unmutated and mutated PCR products are ready, they are linked by overlap extension (by annealing of short complementary oligonucleotide regions incorporated within the back and forward primers of the two PCR reactions). The cDNA containing the entire $V_H$ region is then inserted into the original position of the $V_H$ in pHEN2 vector, yielding a library containing an unmutated $V_L$ domain linked to the mutated $V_H$ domain. The cDNA library is electroporated into TG1 cells and phages displaying the Fv are packaged using helper phage. Phage concentration are determined by coating 100 μl/well of phage samples diluted in 100 mM NaHCO3 pH 8.6 for 45 minutes at 37° C. A phage standard is employed (standard curve ranges from 0.5 pM to 20 pM phages). Wells are washed and then blocked with skim milk in buffer. Wells were washed between each incubation. Detection of coated phages is with rabbit anti-Fd (1:1000) followed by goat anti-rabbit horseradish peroxidase (1:1000). Color is developed with OPD (o-phenylenediamine; Sigma) and reaction was stopped with 10N H2SO4. Plates are read at 490 nm (BioRad plate reader).

The phages (~$10^{12}$) are then subjected to selection for binding to gp120. For screening of selected phages, Nunc Maxisorp plates are coated directly with gp120 or with 10 μg/ml streptavidin (Sigma) followed biotinylated gp120 in 100 mM NaHCO3 pH 9.5 for 1 hour at 37° C. The plates are blocked with skim milk and washed 3 times 2 minutes each with PBS containing 0.1% skim milk between each incubation step. Then Fv clones are incubated in the wells for 1 hour at 37° C. Detection is with anti-c-myc Ab, followed by anti-mouse IgG. Competition ELISAs are performed by conducting Fv incubations in the presence of soluble polypeptides.

The $V_L$ and $V_H$ domains of the resultant Fv constructs are sequenced and the sequences compared with the parental Fv clone to identify the V domain mutations associated with the improved biological activity of the engineered clones. Flow cytometry analysis is useful to confirm the reactivity of the Fv with native HIV. HIV-infected cells are used for this experiment. Staining infected cells is performed using standard methods. Briefly, $5 \times 10^5$ HIV-infected and non-infected, PHA activated PBMC (negative cell control) is incubated with the primary Ab or Ab fragment for 45 minutes on ice followed by 2 washes in PBS. Then appropriate secondary Ab labeled with a fluorescent probe is added and further incubated on ice for 45 minutes followed by washing twice in PBS. Stained cells are then fixed with 0.1% formalin in PBS and stored at 4° C. in the dark until analysis. Flow cytometric analysis is performed by customary methods using side/forward scatter measurements to identify live cells. Controls include uninfected cells as well as nonimmune Abs. The flow cytometry analyses can help determine apparent Ab binding affinities for trimeric gp120 expressed on infected cells. Increasing concentrations of Ab are added to infected cell lines (H9 infected with a lab-adapted strain or PBMC infected with various clades, followed by detection of the bound Ab. Flow cytometry is performed and mean fluorescence intensities are obtained from each concentration of the Ab. Data are fitted to the one site reversible binding model to determine apparent binding affinity.

Avidity of gp120 binding is determined by surface plasmon resonance methods. Briefly, sensor Chip SA from Biacore has a carboxymethylated dextran matrix that is pre-immobilized with streptavidin. Bt-gp120 is incubated with a streptavidin-sensor chip. Then the Abs are flowed across the sensor chip. Sensorgrams are compared amongst the different monomeric and multivalent proteins to determine which molecule binds with the highest avidity.

In addition to the strategy described above, favorable mutations can also be introduced in the V domains on a rational basis to improve the binding affinity (recent example, ref 11), particularly if structural information is available about the antigen-Ab complex. For instance, candidate amino acids suitable for mutagenesis can be identified by molecular modeling or X-ray crystallography information. Molecular modeling of Ab V domains is carried out using combined homology and ab initio algorithmns. Computer programs with strong predictive value for tracing peptide backbone topography have been developed, but side chain positions are more difficult to predict. Modeling is initiated by identifying the database Fab/Fv structure with the greatest sequence homology. Canonical structures for the FRs, VL CDR1-3 and VH CDR1-2 are available. Regions of greatest variability (particularly VH CDR3 loop structure) are iteratively energy minimized under a suitable force field. The ligand can be positioned in the hypothetical binding site to identify candidate residues suitable for rational mutagenesis. For instance, replacement of a small neutral amino acid with a similarly sized charged residue can be attempted as a means to introduce an additional electrostatic stabilizing interaction. Uncertainties regarding the outcome of such attempts relate to the non-rigid character of protein-protein interactions. Binding of antigens is accompanied by conformational changes in the antigen as well as the Ab. Induced conformational transitions are likely to be more profound in the vicinity of the contact residues, but longer range confonnational alterations are not excluded.

$V_L$-$V_H$ hybridization. In addition to Fv clones, L chain clones from lupus libraries displaying the correct specificity for gp120 are available for improvement by engineering methods. Ab V domains can recognize antigens independently of each other, albeit with reduced binding affinity compared to the native combining site formed by the VL and VH domains. The binding activity of the individual VL domains comprising the anti-HIV L chains is improved by searching for compatible VH domains from suitable VH libraries. The feasibility of this approach is suggested by the following considerations: (a) The $V_L$ and the $V_H$ domains are independently capable of binding antigens (12, 13), with the $V_H$ domain providing the major contribution to overall antigen binding specificity (14). An example of this is the improved recognition of the antigen VIP by pairing of a VIP recognizing L chain with its partner VH domain (15). In principle, such an approach could be employed to obtain Abs that are superior to natural antigen-specific Abs. There is no bar to repeated rounds of affinity improvements in vitro. In comparison, biological forces governing B cell development impose upper limits to Ab specificity and affinity in vivo. On the other hand, the ability to manipulate the two V domains separately can be exploited to useful ends.

Individual VH domains from Abs with established gp120-recognizing activity, e.g., Ab clones S1-1 or b12 can be employed as the lupus VL domains partners. Alternatively a library of VH domains is employed to increase the probability of forming appropriate VH domains capable of forming a compatible $V_L$-$V_H$ molecular interface (i.e., an interface that brings the CDRs into sufficient spatial proximity to form a functional catalytic site). The most favorably paired $V_L$-$V_H$ domains are then identified by phage selection methods even if they constitute a minority of the overall combinations. Suitable $V_H$ domain sources are the HIV-1 infected individuals, who produce large amounts of specific anti-gp120 Abs. Another suitable source of VH domains is transgenic mice expressing human Abs that are immunized with gp120 or synthetic gp120(421-436), e.g., Xenomouse™ mice produced by Abgenix Inc. Methods for immunization of these mice are as described by us previously (16), by administration of gp120 or synthetic gp120(421-436) conjugated to carrier proteins. Preparation of Fv libraries from the HIV-infected individuals and the transgenic mice is essentially as described above. Phages expressing Fv are subjected to selection by binding to gp120 or synthetic gp120(421-436) as before, allowing recovery of Fv clones as the source of VH domains. A large proportion of $V_H$ domains from these Fv clones can be anticipated to independently recognize gp120, as suggested by studies that the $V_H$ domain provides a dominant contribution in noncovalent antigen recognition. Such VH domains are suitable as partners for the anti-HIV L chains isolated from lupus patients.

Methods to generate the hybrid Fvs are in place in our lab (15). Essentially, the cDNA of the $V_L$ cDNA is amplified from the vector using primers containing the appropriate restriction sites necessary for cloning into pHEN2 vector containing the Fv constructs. The linker sequence is contained within the vector. Following removal of the endogenous $V_L$ domain cDNA by restriction digestion, the desired $V_L$ domain is ligated into the vector. VH domains from phage DNA selected as in the preceding paragraph (from HIV-1 infected individuals and transgenic mice) are then ligated into the vector, and hybrid Fv phages are packaged. The hybrid phages expressing hybrid Fv are subjected to selection and screening for binding of the appropriate gp120 antigenic preparation. The success of this strategy is reflected as an increase in the gp120 binding and HIV-1 neutralization of the Fv clones compared to the parental L chain.

VL-VH orientations: If needed the orientation of the V domains in the Fv is changed. Some groups investigating Fv binding have not found a significant difference in the ability of Fv to bind antigen in either orientation (VH-VL or VL-VH) (17,18). Briefly, oligonucleotide primers are synthesized to PCR-amplify the VH with Sfi I and Xho I restriction sites such that it can be ligated into the 5' position. Likewise, are synthesized to amplify the VL for ligation 3' of the linker into Apa LI and Not I sites. The Fv in both its orientations is purified and tested for binding to gp120 and neutralization of HIV.

Linker effects: As noted previously, Fv constructs can undergo inter-molecular aggregation (19-21). To determine such effects, the Fv is analyzed by gel filtration columns. Peaks corresponding to each multimeric species are identified by comparison with retention times of standard proteins, and the proportion of Fv existing in monomeric and aggregate state is computed. ELISA studies are conducted as a function of soluble Fv concentration and these results are compared with the concentration dependence of the aggregation phenomenon.

The length and constitution of the linker peptide can exert important effects. Optimization of the linker can be done, for example, by randomization of the linker sequence, followed by identification of the variants showing the desired behavior. An example of one of a preferred strategy for this purpose follows. As retention of linker flexibility is necessary, glycines in the linker are maintained and serines at linker positions 2, 7, 12 and 15 are substituted with all 20 amino acids using a modification of the randomization method of Tang et al. (22). This has the effect of offering a variety of VL-VH interfacial interactions, some of which alleviate aggregation effects and improve functional behavior. Briefly, an oligonucleotide with an Nco I restriction site at the 5' end of the oligo and an Xho I site at the 3' end is synthesized such that the codons corresponding to serines 2, 7, 12 and 15 are randomized and allow incorporation of all 20 amino acids. The diversity of this linker library is 3.2×10⁶. A complementary antisense 15-mer hybridizing with the 3' end of the primer containing an Xho I site is used to generate double stranded linker. This mutagenized linker library is ligated into pHEN2 containing S1-1 VL and VH and used to transform TG-1 cells followed by phage production. The linker library is subjected to selection for binding of gp120 or synthetic gp120 peptides. Screening for HIV neutralization is done as before to identify the best variant.

REFERENCES 1. van de Putte, L. B., Rau, R., Breedveld, F. C., Kalden, J. R., Malaise, M. G., van Riel, P. L., Schattenkirchner, M., Emery, P., Burmester, G. R., Zeidler, H., Moutsopoulos, H. M., Beck, K. and Kupper, H. Efficacy and safety of the fully human anti-tumour necrosis factor alpha monoclonal antibody adalimumab (D2E7) in DMARD refractory patients with rheumatoid arthritis: a 12 week, phase II study. *Ann Rheum Dis.* 62:1168-1177, 2003.
2. Kessler, J. A., McKenna, P. M., Emini, E. A., Chan, C. P., Patel, M. D., Gupta, S. K., Mark, G. E., Barbas, C. F., Burton, D. R. and Conley, A. J. Recombinant human monoclonal antibody IgG1b12 neutralizes diverse human immunodeficiency virus type 1 primary isolates. *AIDS Res Hum Retroviruses.* 13:575-582, 1997.
3. Coloma, M. J., Hastings, A., Wims, L. A. and Morrison, S. L. Novel vectors for the expression of antibody molecules using variable regions generated by polymerase chain reaction. *J Immunol Methods.* 152:89-104, 1992.
4. Shin, S. U. and Morrison, S. L. Production and properties of chimeric antibody molecules. *Methods Enzymol.* 178:459-76, 1989.
5. Paul, S. Protein engineering. In Walker, J. (ed) *Molecular Biotechniques.* Totowa: Humana Press, pp. 547-566, 1998.
6. Brininann, U., Buchner, J. and Pastan, I. Independent domain of *Pseudoinonas* exotoxin and single-chain immunotoxins: influence of interdomain conmections. *Proc Nat Acad Sci USA.* 89:3075-3079, 1992.
7. Yang, W. P., Green, K., Pinz-Sweeney, S., Briones, A. T., Burton, D. R. and Barbas, C. F. CDR walking mutagenesis for the affinity maturation of a potent human anti-HIV-1 antibody into the picomolar range. *J Mol Biol.* 254:392-403, 1995.
8. Barbas, C. F., Bain, J. D., Hoekstra, D. M. and Lerner, R. A. Semisynthetic combinatorial antibody libraries: a chemical solution to the diversity problem. *Proc Natl Acad Sci USA.* 89:4457-4461, 1992.
9. Hoogenboom, H. R. and Winter, G. By-passing immunisation. Human antibodies from synthetic repertoires of germnline VH gene segments rearranged in vitro. *J Mol Biol.* 227:381-388, 1992.
10. Barbas, C. F., Hu, D., Dulop, N., Sawyer, L., Cababa, D., Hendry, R. M., Nara, P. L. and Burton, D. R. In vitro evolution of a neutralizing human antibody to human immunodeficiency virus type 1 to enhance affinity and broaden strain cross-reactivity. *Proc Natl Acad Sci USA.* 91:3809-3813, 1994.
11. Luo, G. X., Kohlstaedt, L. A., Charles, C. H., Gorfain, E., Morantte, I., Williams, J. H. and Fang, F. Humanization of an anti-ICAM-1 antibody with over 50-fold affinity and functional improvement. *J Immnunol Methods.* 275:31-40, 2003.
12. Ward, E. S., Gussow, D., Griffiths, A. D., Jones, P. T. and Winter, G. Binding activities of a repertoire of single immunoglobulin variable domains secreted from *Escherichia coli. Nature.* 341:544-546, 1989.
13. Sun, M., Li, L., Gao, Q. S. and Paul, S. Antigen recognition by an antibody light chain. *J Biol Chem.* 269:734-738, 1994.
14. Davies, D. R. and Chacko, S. Antibody structure. *Acc Chem Res.* 26:421-427, 1993.
15. Sun, M., Gao, Q. S., Kimarskiy, L., Rees, A. and Paul, S. Cleavage specificity of a proteolytic antibody light chain and effects of the heavy chain variable domain. *J Mol Biol.* 271:374-385, 1997.
16. Karle, S., Nishiyama, Y., Zhou, Y. X., Luo, J., Planque, S., Hanson, C. and Paul, S. Carrier-dependent specificity of antibodies to a conserved peptide determinant of gp120. *Vaccine.* 21:1213-1218, 2003.
17. Hamilton, S., Odili, J., Gundogdu, O., Wilson, G. D. and Kupsch, J. M. Improved production by domain inversion of single-chain Fv antibody fragment against high molecular weight proteoglycan for the radioimmunotargeting of melanoma. *Hybrid Hybridonzics,* 20:351-360, 2001.
18. Lawrence, L. J., Kortt, A. A., Iliades, P., Tulloch, P. A. and Hudson, P. J. Orientation of antigen binding sites in dimeric and trimeric single chain Fv antibody fragments. *FEBS Lett.* 425:479-84, 1998.
19. Pluckthun, A. and Skerra, A. Expression of functional antibody Fv and Fab fragments in *Escherichia coli. Methods Enzyinol.* 178:497-515, 1998.
20. Skerra, A. and Pluckthun, A. Assembly of a functional immunoglobulin Fv fragment in *Escherichia coli. Science.* 240:1038-1041, 1988.
21. Worn, A. and Pluckthun, A. Stability Engineering of antibody single-chain Fv fragments. *J Mol Biol.* 305:989-1010, 2001.
22. Tang, Y., Jiang, N., Parakh, C. and Hilvert, D. Selection of linkers for a catalytic single-chain antibody using phage display technology. *J Biol Chein.* 271:15682-15686, 1996.

EXAMPLE 4

Antigenic HERV Identification

Determining the identity of expressible endogenous sequences with homology to residues 421-436 of gp120 in lupus patients is useful for several purposes, including identification of the HERV element(s) driving the synthesis of Abs that recognize gp120 and development of novel vaccine candidates. Examples of the strategies employed for this purpose follow.

Endogenous human sequences homologous to gp120. Increased expression and/or increased immune responsiveness to endogenous retroviral sequences homologous to residues 422-432 is believed to drive the synthesis of Abs that recognize gp120. This is based on previous studies suggesting that residues 421-432 form the core epitope for lupus Ab recognition and new database analyses identifying a genomic HERV-L sequence with partial homology to gp120 residues 422-432. No sequence homology between residues 422-432 and known human proteins is evident, although other regions of gp120 are homologous to certain proteins (1-3).

Initial study of expressible gp120-related sequences is done using MRNA from PBMCs. The main advantage of PBMCs is their availability for comparisons between healthy donors and lupus patients. Certain HERV mRNA species have previously been identified in PBMCs. HERV expression can be tissue specific. If PBMCs do not contain mRNA species encoding the gp120 related sequences, additional tissues can be screened. Alternative sources are commercial eDNA libraries prepared using MRNA from pooled human tissues (e.g., brain, liver, lung; available from ClonTech). An interesting alternative is the use of MRNA from the placentae of healthy and lupus patients. HERV sequences are expressed at high levels in the placenta (4-6), and pregnancy is known to influence the clinical symptoms of autoimmune disease. Full-term placentae are accessible from healthy and lupus subjects with minimal delay after delivery, whereas other tissues must be collected from autopsy or rare biopsy procedures.

Total RNA and MnRNA from healthy individuals and uninfected lupus patients positive for Abs (N=20 each) that bind gp120 at residues 422-432 are prepared by standard phenol extraction and oligo-dT purification methods taking care to minimize ribonuclease digestion of the RNA. Reverse transcriptase-polymerase chain reaction (RT-PCR) is used to amplify the desired cDNA. The forward primer is oligo-dT (15 mer). As examples, the following two back primers are tested: (a) the primer corresponding to the consensus sequence of gp120 residues 422-432 [caaattataaacatgtggcag-gaagtaggaaaa]; and (b) the primer corresponding to the sequence of HERV-L region homologous to gp120 residues 422-432 [caaattaaaaactttttaaagaaagtaggaaaa]. RT-PCRs conducted with PBMCs from HIV+ subjects serves as the positive control. This yields a well defined PCR product because of expression of the gp120 gene in infected cells. Genomic DNA is analyzed in parallel to determine whether nonexpressible sequences homologous to residues 422-432 are present. A primers complementary to a non-expressed gene sequence (e.g., an intron sequence) is used as the negative control to assure specificity of amplification. The reactions are carried out at several temperatures and MgCl2 concentrations to vary annealing permissivity and allow annealing despite partial mismatches with the template. The size of the cDNA product depends on the number of nucleotides in the mRNA separating the poly A tail from the gp120 422-432 region. We have previously applied similar degenerate annealing methods to amplify Ab V sequences, which contain homologous but non-identical 5' ends. Once a well-defined PCR product has been demonstrated, it is sequenced. For this purpose the PCR product is cloned into a suitable vector [e.g., cloning via Sfi I and Not I restriction sites into pCANTAB5His6 followed by conventional didexoynucleotide sequencing]. Homology analyses identifies the gene from which the PCR product is derived [Blastn; HERV database, herv.imq.cas.cz; as noted above, the PCR product corresponds to a gene fragment].

The foregoing strategy allows detection of any endogenous mRNA encoding a peptide determinant homologous to residues 422-432. An alternative approach is to focus exclusively on HERV elements. Numerous HERV sequences have emerged from the human genome project, and an initial systematic organization of HERV sequences into a databases has become available. Close to the 5' terminus of HERV sequences are found short nucleotide stretches homologous to retroviral tRNA binding sites (designated primer binding site or PBS; presumably these sites once served as primers for reverse transcription of the viral genes).Twenty two HERV families are distinguishable based on their resemblance to known retroviruses [e.g., HERV-L members contain a PBS homologous to tRNA$^{Leu}$ and the pol sequence is similar to that of foamy viruses]. Therefore, the alternative experimental approach employs the gp120 residue 422-432 as forward primers and back primers corresponding to the PBS. This method has been applied to identify other expressible HERV elements (4,5,7). The advantage of this approach is that the full-length gene corresponding to the mRNA of interest can be readily cloned once the correct expressible HERV sequence has been identified, i.e., by using the HERV-specific back primer combined with an oligo-dT primer that anneals the poly A tail. The disadvantage is that expression of the gp120 422-432 homolog may occur as a HERV fragment inserted into another gene [in this case the PBS may not be present in the expressed gene].

Quantification of the expressible MRNA: Once the identity of the PCR product corresponding to gp120 residues 422-432 has been confirmed, comparative measurement of mRNA levels in healthy individual and lupus patients is desirable by real-time quantitative RT-PCR [that is, if expression is not restricted to lupus patients]. Briefly, a fluorescently-tagged primer is employed and each PCR cycle results in an increase in fluorescence (measured by hydrolysis of the amplified product) that is directly proportional to the number of product molecules, which in turn is a direct measure of the number of template amplicons. Total RNA from at least 20 healthy and lupus patients each is treated with RNase-free DNase I and serves as template. Primer sequences are based on the cDNA sequence information obtained from the preceding section. The initial few cycles are run using a primer set with a comparatively low Tm. In second phase of the PCR, the fluorescent primer is designed to anneal with a higher Tm. The number of PCR cycles needed to yield reliable signals are standardized. Amplification of an mRNA like β-actin or cyclophilin mRNA is done in parallel.

Further immunological and genetic analyes: Further experimental maneuvers are dictated by the results of the preceding studies. For example, the cDNA identified in the preceding section could correspond to a previously characterized, full-length HERV protein. Another scenario is that a relatively short HERV element homologous to residues 422-432 is inserted into a gene encoding a non-HERV protein. For illustration, following is .a brief description of certain general methods. The gene fragment identified to be homologous to gp120 is radiolabeled with [.sup.32P]dCTP using a commercially available kit and applied as a hybridization probe to screen a cDNA library such as the human leucocyte expression library in .lamda. phagemid available from Clontech [obtained from human RNA pooled from 585 Caucasians; contains long cDNA inserts >3 kbases, mostly corresponding to full-length genes]. If the desired gene is found to be expressed only in lupus patients, a new cDNA library from PBMC of lupus patients is constructed as in (8). Standard hybridization methods can be applied to identify and sequence the clone(s) annealing with the probe, which helps identify the full-length gene encoding the peptide determinant homologous to gp120 residues 422-432. Following confirmation of the presence of an open reading frame www.ncbi.nlm.nih.gov/gorf/gorf.html), the cDNA corresponding to the full-length is recloned in an appropriate expression vector [e.g., baculovirus system to ensure appropriate post-translational processing; a his6 tag can be introduced to allow rapid purification].

At this point, antigenicity and immunogenicity studies become feasible. Two types of studies are done: (a) demonstration of specific recognition of the purified recombinant protein by Fv clones and full-length Abs described in Aim 2 [clones JL413, JL427, GL2, GL59]; and (b) use of the recombinant protein as immunogen to induce monoclonal Abs that neutralize HIV because of specific recognition of gp120 residues 422-432. Methods for this purpose are essentially as described before. Generation of monoclonal Abs is described in our previous publications (e.g. ref 9).

An alternative strategy is the use of a cDNA phage display library expressing mRNA isolated from lupus patients. This strategy allows screening of the library for antigens reactive with the gp120-specific Abs isolated previously from lupus patients. However, this approach suffers from several technical pitfalls, including difficulties in ensuring expression of large full-length proteins in native conformation on the phage surface.

In view of the unique properties of lupus Abs, identification of the underlying immunogen driving their synthesis may help advance anti-HIV vaccine design. It is reasonable to assume that such an immunogen must exist to support maturation of B cells responsible for specific Ab synthesis. This is supported by the presence of extensive replacement mutations clustered in the CDRs of lupus Abs that recognize gp120 [compared to the FRs], a hallmark of adaptively-matured V genes.

REFERENCES

1. De Santis, C., Robbioni, P., Longhi, R., Lopalco, L., Siccardi, A. G., Beretta, A. and Roberts Jr., N. J. Cross-reactive response to human immunodeficiency virus type 1 (HIV-1) gp120 and HLA class I heavy chains induced by receipt of HIV-1-derived envelope vaccines. *J Infect Dis.* 168:1396-1403, 1993.
2. Pert, C. B., Hill, J. M., Ruff, M. R., Berman, R. M., Robey, W. G., Arthur, L. O., Ruscetti, F. W. and Farrar, W. L. Octapeptides deduced from the neuropeptide receptor-like pattern of antigen T4 in brain potently inhibit human immunodeficiency virus receptor binding and T-cell infectivity. *Proc Natl Acad Sci USA.* 83:9254-9258, 1986.
3. Lee, M. R., Ho, D. D. and Gurney, M. E. Functional interaction and partial homology between human immunodeficiency virus and neuroleukin. *Science.* 237:1047-1051, 1987.
4. Nelson, P. N., Carnegie, P. R., Martin, J., Davari Ejtehadi, H., Hooley, P., Roden, D., Rowland-Jones, S., Warren, P., Astley, J. and Murray, P. G. Demystified—Human endogenous retroviruses. *Mol Pathol.* 56:11-18, 2003.
5. Urnovitz, H. B. and Murphy, W. H. Human endogenous retroviruses: nature, occurrence, and clinical implications in human disease. *Clin Microbiol Rev.* 9:72-99, 1996.
6. Langat, D. K., Johnson, P. M., Rote, N. S., Wango, E. O., Owiti, G. O., Isahakia, M. A. and Mwenda, J. M. Characterization of antigens expressed in normal baboon trophoblast and cross-reactive with HIV/SIV antibodies. *J Reprod Immunol.* 42:41-58, 1999.
7. Tristem, M. Identification and characterization of novel human endogenous retrovirus families by phylogenetic screening of the human genome mapping project database. *J Virol.* 74:3715-3730, 2000.
8. Yamano, S., Nhamburo, P. T., Aoyama, T., Meyer, U. A., Inaba, T., Kalow, W., Gelboin, H. V., McBride, O. W. and Gonzalez, F. J. eDNA cloning, sequence and cDNA-directed expression of human P450IIBV1: Identification of a normal and two variant cDNAs derived from the CYP2B Locus on chromosome19 and differential expression of the IIIB mRNAs in human liver. *Biochemistry.* 28:7340-7348, 1989.
9. Paul, S., Planque, S., Zhou, Y.-X., Taguchi, H., Bhatia, G., Karle, S., Hanson, C. and Nishiyama, Y. Specific HIV gp120 cleaving antibodies induced by covalently reactive analog of gp120. *J Biol Chem.* 278:20429-20435, 2003.

The invention claimed is:

1. An isolated monoclonal antibody or fragment thereof, comprising a light chain variable ($V_L$) domain comprising an amino acid sequence selected from the group consisting of SEQ ID NO:43, SEQ ID NO:44 and SEQ ID NO:46, wherein said isolated monoclonal antibody or fragment thereof binds to gp120 and gp120(421-436).

2. The isolated monoclonal antibody or fragment thereof of claim 1, which is an $F_V$ or single chain $F_V$ (sc$F_V$) fragment.

3. The isolated monoclonal antibody or fragment thereof of claim 1, comprising:
   a light chain variable ($V_L$) domain comprising SEQ ID NO:44; and
   a heavy chain variable ($V_H$) domain comprising SEQ ID NO:45.

4. The isolated monoclonal antibody or fragment thereof of claim , which is an $F_V$ or single chain $F_V$ (sc$F_V$) fragment.

5. The isolated monoclonal antibody or fragment thereof of claim 1, comprising:
   a light chain variable ($V_L$) domain comprising SEQ ID NO:46; and
   a heavy chain variable ($V_H$) domain comprising SEQ ID NO:47.

6. The isolated monoclonal antibody or fragment thereof of claim 5, which is an $F_V$ or single chain $F_V$ (sc$F_V$) fragment.

7. The isolated monoclonal antibody or fragment thereof of claim 1, comprising a light chain variable ($V_L$) domain comprising SEQ ID NO:43.

8. The isolated monoclonal antibody or fragment thereof of claim 7, which is an $F_V$ or single chain $F_V$ (sc$F_V$) fragment.

9. An isolated monoclonal antibody or fragment thereof comprising:
   a heavy chain variable ($V_H$) domain comprising an amino acid sequence selected from the group consisting of SEQ ID NO:45 and SEQ ID NO:47.

10. The isolated monoclonal antibody or fragment thereof claim 9, which is an $F_V$ or single chain $F_V$ (sc$F_V$) fragment.

11. A composition comprising the isolated monoclonal antibody or fragment thereof of claim 1 and a pharmaceutical carrier.

12. A composition comprising the isolated carrier monoclonal antibody or fragment thereof of claim 3 and a pharmaceutical carrier.

13. A composition for prophylaxis or therapy of HIV comprising the isolated monoclonal antibody or fragment thereof of claim 5 and a pharmaceutical carrier.

14. A composition comprising the isolated monoclonat antibody or fragment thereof of claim 7 and a pharmaceutical carrier.

15. A composition comprising the isolated monoclonal antibody or fragment thereof of claim 9 and a pharmaceutical carrier.

* * * * *

```
                             SEQUENCE LISTING

<160> NUMBER OF SEQ ID NOS: 66

<210> SEQ ID NO 1
<211> LENGTH: 48
<212> TYPE: DNA
<213> ORGANISM: Human immunodeficiency virus type 1

<400> SEQUENCE: 1
aaacaaatta taaacatgtg gcaggaagta ggaaaagcaa tgtatgcc                    48

<210> SEQ ID NO 2
<211> LENGTH: 48
<212> TYPE: DNA
<213> ORGANISM: Human immunodeficiency virus type 1

<400> SEQUENCE: 2
ggcatacatt gcttttccta cttcctgcca catgtttata atttgttt                    48

<210> SEQ ID NO 3
<211> LENGTH: 48
<212> TYPE: DNA
<213> ORGANISM: Human immunodeficiency virus type 1

<400> SEQUENCE: 3
aaacaaatta taaacatgtg gcaggaagta ggaaaagcaa tgtatgcc                    48

<210> SEQ ID NO 4
<211> LENGTH: 48
```

```
<212> TYPE: DNA
<213> ORGANISM: Human immunodeficiency virus type 1

<400> SEQUENCE: 4
ggcatacatt gcttttccta cttcctgcca catgtttata atttgttt            48

<210> SEQ ID NO 5
<211> LENGTH: 16
<212> TYPE: PRT
<213> ORGANISM: Human immunodeficiency virus type 1

<400> SEQUENCE: 5

Lys Gln Ile Ile Asn Met Trp Gln Glu Val Gly Lys Ala Met Tyr Ala
 1               5                  10                  15

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Linker
      peptide

<400> SEQUENCE: 6

Ser Ser Gly Gly Gly Gly Ser Gly Gly Gly Gly Ser Gly Gly Ser Ala
 1               5                  10                  15

<210> SEQ ID NO 7
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 7
gtcctcgcaa ctgcggccca gccggccatg gccgacatcc agatgaccca gtctcc     56

<210> SEQ ID NO 8
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 8
gtcctcgcaa ctgcggccca gccggccatg gccgatgttg tgatgactca gtctcc     56

<210> SEQ ID NO 9
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 9
gtcctcgcaa ctgcggccca gccggccatg gccgaaattg tgttgacgca gtctcc     56

<210> SEQ ID NO 10
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 10
gtcctcgcaa ctgcggccca gccggccatg gccgacatcg tgatgaccca gtctcc     56
```

```
<210> SEQ ID NO 11
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 11
gtcctcgcaa ctgcggccca gccggccatg gccgaaacga cactcacgca gtctcc      56

<210> SEQ ID NO 12
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 12
gtcctcgcaa ctgcggccca gccggccatg gccgaaattg tgctgactca gtctcc      56

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 13
ccatcctgcg gccgcacact ctcccctgtt gaagctctt                          39

<210> SEQ ID NO 14
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 14
gcctgaaccg cctccaccac tcgagcgttt gatttccacc ttggtccc                48

<210> SEQ ID NO 15
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 15
gcctgaaccg cctccaccac tcgagcgttt gatctccagc ttggtccc                48

<210> SEQ ID NO 16
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 16
gcctgaaccg cctccaccac tcgagcgttt gatatccact ttggtccc                48

<210> SEQ ID NO 17
<211> LENGTH: 48
<212> TYPE: DNA
<213> ORGANISM: Artificial Sequence
<220> FEATURE:
<223> OTHER INFORMATION: Description of Artificial Sequence: Primer
```

-continued

<400> SEQUENCE: 17
gcctgaaccg cctccaccac tcgagcgttt gatctccacc ttggtccc         48

<210> SEQ ID NO 18
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 18
gcctgaaccg cctccaccac tcgagcgttt aatctccagt cgtgtccc         48

<210> SEQ ID NO 19
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 19
gtcctcgcaa ctgcggccca gccggccatg gcccagtctg tgttgacgca gccgcc    56

<210> SEQ ID NO 20
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 20
gtcctcgcaa ctgcggccca gccggccatg gcccagtctg ccctgactca gcctgc    56

<210> SEQ ID NO 21
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 21
gtcctcgcaa ctgcggccca gccggccatg gcctcctatg tgctgactca gccacc    56

<210> SEQ ID NO 22
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 22
gtcctcgcaa ctgcggccca gccggccatg gcctcttctg agctgactca ggaccc    56

<210> SEQ ID NO 23
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 23
gtcctcgcaa ctgcggccca gccggccatg gcccacgtta tactgactca accgcc    56

<210> SEQ ID NO 24
<211> LENGTH: 56
<212> TYPE: DNA

```
<213> ORGANISM: Artificial Sequence
<220> FEATURE:
<223> OTHER INFORMATION: Description of Artificial Sequence: Primer

<400> SEQUENCE: 24
gtcctcgcaa ctgcggccca gccggccatg gcccaggctg tgctcactca gccgtc        56

<210> SEQ ID NO 25
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 25
gtcctcgcaa ctgcggccca gccggccatg gccaatttta tgctgactca gccccca       56

<210> SEQ ID NO 26
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 26
gcctgaaccg cctccaccac tcgagcctag gacggtgacc ttggtccc                 48

<210> SEQ ID NO 27
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 27
gcctgaaccg cctccaccac tcgagcctag gacggtcagc ttggtccc                 48

<210> SEQ ID NO 28
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 28
gcctgaaccg cctccaccac tcgagcctaa aacggtgagc tgggtccc                 48

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 29
tgaagattct gtagggggcca ctgtctt                                        27

<210> SEQ ID NO 30
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 30
catgaccaca gtgcacttca ggtgcagctg gtgcagtctg g                        41
```

<210> SEQ ID NO 31
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 31
catgaccaca gtgcacttca ggtcaactta agggagtctg g          41

<210> SEQ ID NO 32
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 32
catgaccaca gtgcacttga ggtgcagctg gtggagtctg g          41

<210> SEQ ID NO 33
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 33
catgaccaca gtgcacttca ggtgcagctg caggagtcgg g          41

<210> SEQ ID NO 34
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 34
catgaccaca gtgcacttca ggtgcagctg ttgcagtctg c          41

<210> SEQ ID NO 35
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 35
catgaccaca gtgcacttca ggtacagctg cagcagtcag g          41

<210> SEQ ID NO 36
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 36
gagtcattct gcggccgcgg ggaagacsga tgggcccttg gt          42

<210> SEQ ID NO 37
<211> LENGTH: 42
<212> TYPE: DNA
<213> ORGANISM: Artificial Sequence
<220> FEATURE:
<223> OTHER INFORMATION: Description of Artificial Sequence: Primer -continued

```
<400> SEQUENCE: 37
gagtcattct gcggccgcgg ggaaaagggt tggggcggat gc                          42

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Lys Gln Ile Ile Asn Met Trp Gln Glu Val Gly Lys Ala Met Tyr Ala
 1               5                  10                  15

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 39
caaattataa acatgtggca ggaagtagga aaa                                    33

<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 40
caaattaaaa acttttaaa gaaagtagga aaa                                    33

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Ile Lys Asn Phe Leu Lys Glu Val Gly Lys Val Val Tyr Ile
 1               5                  10                  15

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Lys Gly Gly Lys Ala Thr Tyr Ser
 1               5

<210> SEQ ID NO 43
<211> LENGTH: 107
<212> TYPE: PRT
<213> ORGANISM: Artificial Sequence
<220> FEATURE:
<223> OTHER INFORMATION: Description of Artificial Sequence: Light chain
      SK18 VL domain

<400> SEQUENCE: 43
```

```
Asp Ile Gln Met Thr Gln Ser Pro Ser Leu Ser Ala Ser Val Gly
 1               5                  10                  15

Asp Arg Val Thr Val Thr Cys Arg Ala Ser Gln Ser Ile Ser Ser Tyr
             20                  25                  30

Leu Asn Trp Tyr Gln Gln Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65              70                  75                  80

Glu Asp Phe Ala Thr Tyr Phe Cys Gln Gln Ser Tyr Ser Ile Pro Arg
                 85                  90                  95

Thr Phe Gly Gln Gly Thr Lys Val Glu Ile Lys
             100                 105
```

<210> SEQ ID NO 44
<211> LENGTH: 111
<212> TYPE: PRT
<213> ORGANISM: Artificial Sequence
<220> FEATURE:
<223> OTHER INFORMATION: Description of Artificial Sequence: scFv JL427
      VL domain

<400> SEQUENCE: 44

```
Gln Ser Val Leu Thr Gln Pro Pro Ser Val Ser Gly Ala Pro Gly Gln
 1               5                  10                  15

Arg Val Thr Ile Ser Cys Ser Gly Ser Ser Ser Asn Phe Gly Leu Asn
             20                  25                  30

Tyr Val Thr Trp Gln Gly His Phe Pro Gly Thr Ala Pro Lys Leu Leu
         35                  40                  45

Ile Tyr Arg Asn Asp Gln Arg Pro Leu Gly Val Pro Ala Arg Phe Ser
 50                  55                  60

Gly Ser Lys Ser Gly Thr Ser Ala Ser Leu Ala Ile Ser Gly Leu Arg
 65              70                  75                  80

Ser Glu Asp Glu Ala Asp Tyr Tyr Cys Gln Ser Tyr Asp Asn Ser Leu
                 85                  90                  95

Ser Gly Trp Val Phe Gly Gly Gly Tyr Gln Leu Tyr Val Leu Gly
             100                 105                 110
```

<210> SEQ ID NO 45
<211> LENGTH: 118
<212> TYPE: PRT
<213> ORGANISM: Artificial Sequence
<220> FEATURE:
<223> OTHER INFORMATION: Description of Artificial Sequence: scFv JL427
      VH domain

<400> SEQUENCE: 45

```
Gln Val Gln Leu Gln Gln Ser Gly Gly Gly Leu Val Gln Pro Gly Arg
 1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ser Tyr Ile Gly Arg Ser Gly Ser His Thr Asn Tyr Ala Asp Ser Val
 50                  55                  60

Lys Gly Arg Phe Thr Ile Ser Arg Asp Asn Ser Lys Asn Thr Leu Tyr
 65              70                  75                  80
```

```
Leu Gln Ile Asn Ser Leu Arg Ala Glu Asp Thr Ala Val Tyr Tyr Cys
                 85                  90                  95

Ala Arg Gly Leu Pro Asn Tyr Gly Met Asp Ile Trp Gly Gln Gly Thr
            100                 105                 110

Thr Val Thr Val Ser Ser
        115

<210> SEQ ID NO 46
<211> LENGTH: 106
<212> TYPE: PRT
<213> ORGANISM: Artificial Sequence
<220> FEATURE:
<223> OTHER INFORMATION: Description of Artificial Sequence: scFv JL413
      VL domain

<400> SEQUENCE: 46

Asp Val Val Met Thr Gln Ser Pro Ser Ser Val Ser Ala Ser Val Gly
  1               5                  10                  15

Asp Arg Val Thr Ile Thr Cys Arg Ala Ser Gln Gly Ile Gly Asn Trp
             20                  25                  30

Leu Ala Trp Tyr Gln Gln Lys Pro Gly Lys Ala His Asn Leu Leu Ile
         35                  40                  45

Tyr Gly Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Ser Ala Thr Tyr Tyr Cys Gln Gln Ala Leu Val Gly Thr Phe
                 85                  90                  95

Gly Gly Gly Thr Lys Val Glu Ile Lys Ala
            100                 105

<210> SEQ ID NO 47
<211> LENGTH: 107
<212> TYPE: PRT
<213> ORGANISM: Artificial Sequence
<220> FEATURE:
<223> OTHER INFORMATION: Description of Artificial Sequence: scFv JL413
      VH domain

<400> SEQUENCE: 47

Gln Val Asn Leu Arg Glu Ser Gly Pro Gly Leu Val Lys Pro Ser Glu
  1               5                  10                  15

Thr Leu Ser Leu Thr Cys Thr Val Ser Gly Gly Phe Ile Ser Ser Tyr
             20                  25                  30

Tyr Trp Ser Trp Ile Arg Gln Pro Pro Gly Lys Gly Leu Glu Trp Ile
         35                  40                  45

Gly Phe Thr Tyr Tyr Ser Gly Ser Thr Tyr Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Met Tyr Cys Tyr Cys
                 85                  90                  95

Trp Gly Gln Gly Thr Leu Val Thr Val Ser Ser
            100                 105

<210> SEQ ID NO 48
<211> LENGTH: 15
<212> TYPE: PRT
<213> ORGANISM: Human immunodeficiency virus type 1

<400> SEQUENCE: 48
```

Lys Gln Ile Ile Asn Met Trp Gln Glu Val Gly Lys Ala Met Tyr
1               5                   10                  15

<210> SEQ ID NO 49
<211> LENGTH: 15
<212> TYPE: PRT
<213> ORGANISM: Human immunodeficiency virus type 1

<400> SEQUENCE: 49

Lys Gln Ile Ile Asn Met Trp Gln Arg Ala Gly Gln Ala Ile Tyr
1               5                   10                  15

<210> SEQ ID NO 50
<211> LENGTH: 15
<212> TYPE: PRT
<213> ORGANISM: Human immunodeficiency virus type 1

<400> SEQUENCE: 50

Arg Gln Ile Ile Asn Leu Trp Gln Arg Thr Gly Gln Ala Ile Tyr
1               5                   10                  15

<210> SEQ ID NO 51
<211> LENGTH: 15
<212> TYPE: PRT
<213> ORGANISM: Human immunodeficiency virus type 1

<400> SEQUENCE: 51

Lys Gln Ile Ile Asn Met Trp Gln Glu Val Gly Lys Ala Met Tyr
1               5                   10                  15

<210> SEQ ID NO 52
<211> LENGTH: 15
<212> TYPE: PRT
<213> ORGANISM: Human immunodeficiency virus type 1

<400> SEQUENCE: 52

Lys Gln Ile Val Asn Leu Trp Gln Glu Val Gly Lys Ala Met Tyr
1               5                   10                  15

<210> SEQ ID NO 53
<211> LENGTH: 15
<212> TYPE: PRT
<213> ORGANISM: Human immunodeficiency virus type 1

<400> SEQUENCE: 53

Lys Gln Ile Ile Asn Met Trp Gln Gly Val Gly Arg Ala Met Tyr
1               5                   10                  15

<210> SEQ ID NO 54
<211> LENGTH: 15
<212> TYPE: PRT
<213> ORGANISM: Human immunodeficiency virus type 1

<400> SEQUENCE: 54

Lys Gln Ile Val Asn Met Trp Gln Gly Val Gly Arg Ala Thr Tyr
1               5                   10                  15

<210> SEQ ID NO 55
<211> LENGTH: 15
<212> TYPE: PRT
<213> ORGANISM: Human immunodeficiency virus type 1

<400> SEQUENCE: 55

Lys Gln Ile Ile Asn Met Trp Gln Glu Val Gly Lys Ala Met Tyr
1               5                   10                  15

```
<210> SEQ ID NO 56
<211> LENGTH: 15
<212> TYPE: PRT
<213> ORGANISM: Human immunodeficiency virus type 1

<400> SEQUENCE: 56

Lys Gln Ile Ile Asn Met Trp Gln Gly Val Gly Lys Ala Met Tyr
 1               5                  10                  15

<210> SEQ ID NO 57
<211> LENGTH: 15
<212> TYPE: PRT
<213> ORGANISM: Human immunodeficiency virus type 1

<400> SEQUENCE: 57

Arg Gln Ile Val Asn Met Trp Gln Glu Val Gly Arg Ala Met Tyr
 1               5                  10                  15

<210> SEQ ID NO 58
<211> LENGTH: 15
<212> TYPE: PRT
<213> ORGANISM: Human immunodeficiency virus type 1

<400> SEQUENCE: 58

Lys Gln Ile Val Asn Met Trp Gln Gly Val Gly Arg Ala Met Tyr
 1               5                  10                  15

<210> SEQ ID NO 59
<211> LENGTH: 15
<212> TYPE: PRT
<213> ORGANISM: Human immunodeficiency virus type 1

<400> SEQUENCE: 59

Lys Gln Ile Val Arg Met Trp Gln Arg Val Gly Gln Ala Met Tyr
 1               5                  10                  15

<210> SEQ ID NO 60
<211> LENGTH: 15
<212> TYPE: PRT
<213> ORGANISM: Human immunodeficiency virus type 1

<400> SEQUENCE: 60

Lys Gln Ile Val Asn Met Trp Gln Arg Val Gly Gln Ala Met Tyr
 1               5                  10                  15

<210> SEQ ID NO 61
<211> LENGTH: 15
<212> TYPE: PRT
<213> ORGANISM: Human immunodeficiency virus type 1

<400> SEQUENCE: 61

Lys Gln Ile Val Arg Met Trp Gln Arg Thr Gly Gln Ala Ile Tyr
 1               5                  10                  15

<210> SEQ ID NO 62
<211> LENGTH: 15
<212> TYPE: PRT
<213> ORGANISM: Human immunodeficiency virus type 1

<400> SEQUENCE: 62

Lys Gln Ile Ile Asn Met Trp Gln Lys Val Gly Gln Ala Ile Tyr
 1               5                  10                  15

<210> SEQ ID NO 63
```

```
<211> LENGTH: 15
<212> TYPE: PRT
<213> ORGANISM: Human immunodeficiency virus type 1

<400> SEQUENCE: 63

Arg Gln Ile Val Asn Leu Trp Thr Arg Val Gly Lys Gly Ile Tyr
 1               5                  10                  15

<210> SEQ ID NO 64
<211> LENGTH: 15
<212> TYPE: PRT
<213> ORGANISM: Human immunodeficiency virus type 1

<400> SEQUENCE: 64

Arg Gln Val Val Arg Ser Trp Ile Arg Gly Gln Ser Gly Leu Tyr
 1               5                  10                  15

<210> SEQ ID NO 65
<211> LENGTH: 33
<212> TYPE: DNA
<213> ORGANISM: Human immunodeficiency virus type 1

<400> SEQUENCE: 65
caaattataa acatgtggca gaaagtagga aaa                              33

<210> SEQ ID NO 66
<211> LENGTH: 33
<212> TYPE: DNA
<213> ORGANISM: Artificial Sequence
<220> FEATURE:
<223> OTHER INFORMATION: Description of Artificial Sequence: synthetic
      rv_85283 polynucleotide sequence

<400> SEQUENCE: 66
caaattaaaa acttttaaa gaaagtagga aaa                               33
```